(12) United States Patent
Rosen et al.

(10) Patent No.: US 9,417,247 B2
(45) Date of Patent: Aug. 16, 2016

(54) HUMAN AUTOANTIBODIES SPECIFIC FOR PAD3 WHICH ARE CROSS-REACTIVE WITH PAD4 AND THEIR USE IN THE DIAGNOSIS AND TREATMENT OF RHEUMATOID ARTHRITIS AND RELATED DISEASES

(71) Applicant: The Johns Hopkins University, Baltimore, MD (US)

(72) Inventors: Antony Rosen, Pikesville, MD (US); Erika Lynn Darrah, Baltimore, MD (US); Felipe Andrade, Timonium, MD (US); Jon Tyler Giles, New York, NY (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 14/617,412

(22) Filed: Feb. 9, 2015

(65) Prior Publication Data

US 2015/0198609 A1 Jul. 16, 2015

Related U.S. Application Data

(62) Division of application No. 14/071,996, filed on Nov. 5, 2013, now Pat. No. 8,975,033.

(60) Provisional application No. 61/722,306, filed on Nov. 5, 2012.

(51) Int. Cl.
*G01N 33/53* (2006.01)
*G01N 33/68* (2006.01)
*G01N 33/564* (2006.01)

(52) U.S. Cl.
CPC ............ *G01N 33/686* (2013.01); *G01N 33/564* (2013.01); *G01N 2333/978* (2013.01); *G01N 2800/102* (2013.01); *G01N 2800/12* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 5,225,539 A | 7/1993 | Winter | |
| 5,449,752 A | 9/1995 | Fujii | |
| 5,545,806 A | 8/1996 | Lonberg | |
| 5,569,825 A | 10/1996 | Lonberg | |
| 5,585,089 A | 12/1996 | Queen | |
| 5,639,641 A | 6/1997 | Pedersen | |
| 5,693,761 A | 12/1997 | Queen | |
| 5,714,352 A | 2/1998 | Jakobovits | |
| 6,265,150 B1 | 7/2001 | Terstappen | |
| 2002/0197266 A1 | 12/2002 | Debinski | |

OTHER PUBLICATIONS

Darrah et al. Ann Rheum Dis 2012 vol. 71, p. 92-98.*
Auger et al (2010) Rheumatoid arthritis-specific autoantibodies to peptidyl arginine deiminase type 4 inhibit citrullination of fibrinogen. Arthritis Rheum. Jan. 2010;62(1):126-31. doi: 10.1002/art.27230.
Willis et al (2011) N-α-benzoyl-N5-(2-chloro-l-iminoethyl)-L-ornithine amide, a protein arginine deiminase inhibitor, reduces the severity of murine collagen-induced arthritis. J Immunol. Apr. 1, 2011;186(7):4396-404. doi: 10.4049/immunol.1001620. Epub Feb. 23, 2011.
Pollmann et al (2012) Anti-PAD4 autoantibodies in rheumatoid arthritis: levels in serum over time and impact on PAD4 activity as measured with a small synthetic substrate. Rheumatol Int. May 2012;32(5):1271-6. doi: 10.1007/s00296-010-1765-y. Epub Jan. 26, 2011.
Robertson et al (1981) Ionized calcium in body fluids. Crit Rev Clin Lab Sci. 1981;15(2):85-125.
Kearney et al (2005) Kinetic characterization of protein arginine deiminase 4: a transcriptional corepressor implicated in the onset and progression of rheumatoid arthritis. Biochemistry. Aug. 9, 2005;44(31)10570-82..
Arita et al (2004) Structural basis for Ca(2+)-induced activation of human PAD4. Nat Struct Mol Biol. Aug. 2004;11(8):777-83. Epub Jul. 11, 2004.
Harris et al (2008) Association of autoimmunity to peptidyl arginine deiminase type 4 with genotype and disease severity in rheumatoid arthritis. Arthritis Rheum. Jul. 2008;58(7):1958-67. doi: 10.1002/art.23596.
Knuckley et al (2010) Substrate specificity and kinetic studies of PADs 1, 3, and 4 identify potent and selective inhibitors of protein arginine deiminase 3. Biochemistry. Jun. 15, 2010;49(23):4852-63. doi: 10.1021/bi100363t.
Hermansson et al (2010) MS analysis of rheumatoid arthritic synovial tissue identifies specific citrullination sites on fibrinogen. Proteomics Clin Appl. May 2010;4(5):511-8. doi: 10.1002/prca.200900088. Epub Jan. 25, 2010.
Unno et al (2012) Crystallization and preliminary X-ray crystallographic analysis of human peptidylarginine deiminase type III. Acta Crystallogr Sect F Struct Biol Cryst Commun. Jun. 1, 2012;68(Pt 6):668-70. doi: 10.1107/S1744309112015333. Epub May 23, 2012.

(Continued)

*Primary Examiner* — Jacob Cheu
(74) *Attorney, Agent, or Firm* — John Hopkins Technology Transfer

(57) ABSTRACT

In one or more embodiments, the present invention provides a novel biomarker which provides a link between a distinct clinical phenotype and a biochemical effect of an autoantibody on an enzyme implicated in disease pathogenesis. In particular, the present invention provides an isolated or purified human autoantibody to PAD3 protein. Methods of diagnosis of subjects for rheumatoid arthritis (RA) using these antibodies as well as diagnosis of the severity of RA in the subject, and methods for monitoring treatment of a subject with RA are also provided. The biomarkers provided herein are also useful in the diagnosis of connective tissue-interstitial lung disease (CT-ILD) in patients having or suspected of having RA.

9 Claims, 12 Drawing Sheets

(56) References Cited

OTHER PUBLICATIONS

Darrah et al (2012) Peptidylarginine deiminase 2, 3 and 4 have distinct specificities against cellular substrates: novel insights into autoantigen selection in rheumatoid arthritis. Ann Rheum Dis. Jan. 2012;71(1):92-8. doi: 10.1136/ard2011.151712. Epub Aug. 21, 2011.

Kohler et al (1976) Derivation of specific antibody-producing tissue culture and tumor lines by cell fusion. Eur J Immunol. Jul. 1976;6(7):511-9.

* cited by examiner

FIG. 10

TABLE.5 PATIENT CHARACTERISTICS ACCORDING TO PAD3/PAD4 ANTIBODY STATUS

| CHARACTERISTIC | TOTAL (n=176) | NO ANTI-PAD3 OR 4 (n=120) | ANTI-PAD4 ONLY (n=37) | ANTI-PAD3/PAD4 (n=19) | P |
|---|---|---|---|---|---|
| AGE, YEARS | 59±9 | 59±8 | 58±9 | 62±7 | 0.091 |
| MALE, n (%) | 71(40) | 43(36) | 21(57) | 8(42) | 0.60 |
| CAUCASION, n(%) | 152(86) | 101(84) | 35(95) | 16(84) | 0.99 |
| ANY COLLEGE, n(%) | 133(76) | 86(72) | 31(84) | 16(84) | 0.25 |
| EVER SMOKING, n(%) | 105(60) | 80(67) | 16(43) | 10(53) | 0.23 |
| CURRENT SMOKING, n(%) | 20(11) | 19(16) | 2(5) | 0(0) | 0.075 |
| REPORTED LUNG DISEASE, (n=168), n(%) | 27(16) | 22(19) | 4(12) | 1(6) | 0.30 |
| RA DURATION, YEARS | 8(4-17) | 7(4-12) | 15(7-23) | 20(11-28) | <0.001 |
| RF OR ANTI-CCP SEROPOSITIVITY, n(%) | 137(78) | 87(73) | 33(89) | 18(95) | 0.043 |
| ANY SHARED EPITOPE ALLELS, n(%) | 122(70) | 79(67) | 30(81) | 14(74) | 0.79 |
| DAS28-CRP | 3.7(2.9-4.4) | 3.6(2.9-4.3) | 3.5(2.8-4.5) | 3.8(3.3-4.3) | 0.68 |
| CRP, mg/L | 2.4(1.1-7.7) | 2.1(1.0-7.1) | 3.5(1.5-9.5) | 2.0(1.6-5.4) | 0.65 |
| IL-6, pg/mL | 3.7(1.8-7.8) | 3.6(1.7-8.1) | 3.9(1.8-6.3) | 3.7(2.4-9.0) | 0.24 |
| TOTAL SHS | 8(1-37) | 5(0-19) | 12(2-43) | 56(14-132) | <0.001 |
| PAIN (100mm VAS) | 21(9-41) | 21(8-40) | 23(10-41) | 20(5-47) | 0.71 |
| HAQ (0-3) | 0.63(0.12-1.25) | 0.63(0.12-1.25) | 0.75(0.12-1.25) | 0.75(0-1.88) | 0.73 |
| CURRENT PREDNISONE, n(%) | 67(38) | 45(38) | 13(35) | 9(47) | 0.41 |
| CURRENT NON-BIOLOGIC DMARDS, n(%) | 150(86) | 100(84) | 34(92) | 16(84) | 0.99 |
| METHOTREXATE, n(%) | 114(65) | 79(66) | 22(59) | 13(68) | 0.83 |
| LEFLUNOMIDE, n(%) | 19(11) | 11(9) | 5(14) | 3(16) | 0.41 |
| CURRENT BIOLOGICAL DMARDS, n(%) | 81(46) | 55(46) | 17(46) | 10(53) | 0.63 |
| TNF INHIBITORS, n(%) | 78(45) | 52(44) | 17(46) | 10(53) | 0.62 |
| NUMBER OF FAILED DMARDS | 1(0-2) | 1(0-2) | 1(0-3) | 2(0-2) | 0.75 |
| ANY CT-ILD, n(%) | 58(33) | 35(29) | 10(27) | 13(68) | 0.001 |
| ANY GGO, n(%) | 22(13) | 11(10) | 6(16) | 5(28) | 0.047 |
| ANY R/TB/HC, n(%) | 36(22) | 21(19) | 8(22) | 7(39) | 0.045 |
| CT ILD SCORE, UNITS (0-32) | 0(0-2; RANGE 0-10) | 0(0-2; RANGE 0-6) | 0(0-2; RANGE 0-10) | 2(0-2; RANGE 0-10) | 0.020 |
| CT EMHPYSEMA SCORE, UNITS (0-32) | 0(0-0; RANGE 0-6) | 0(0-0; RANGE 0-6) | 0(0-0; RANGE 0-4) | 0(0-0; RANGE 0-2) | 0.77 |
| ANY PFT ABNORMAILTY (n=158), n(%) | 44(28) | 33(29) | 9(29) | 2(13) | 0.23 |
| ANY PFT RESTRICTION OR IMPAIRED DIFF., n(%) | 30(21) | 21(22) | 8(27) | 1(8) | 0.46 |
| ANY RESPIRATORY SYMPTOMS (n=168), n(%) | 69(41) | 47(40) | 13(38) | 9(53) | 0.43 |
| NUMBER OF RESPIRATORY SYMPTOMS | 0(0-1; RANGE 0-4) | 0(-1; RANGE 0-4) | 0(0-2; RANGE 0-4) | 1(0-1; RANGE 0-3) | 0.55 |

FIGURE 11

Table 6. Patient Characteristics According to the Presence of CT-ILD Features

| Characteristic | No CT-ILD (n = 118) | Any CT-ILD (n = 58) | p |
|---|---|---|---|
| Age, years | 58 ± 8 | 61 ± 9 | 0.071 |
| Male, n (%) | 43 (36) | 29 (50) | 0.085 |
| Caucasian, n (%) | 101 (86) | 51 (88) | 0.67 |
| Any college, n (%) | 87 (74) | 46 (79) | 0.42 |
| Ever smoking, n (%) | 62 (53) | 44 (76) | 0.003 |
| Current smoking, n (%) | 7 (6) | 14 (24) | <0.001 |
| Reported lung disease (n=168), n (%) | 19 (17) | 8 (14) | 0.66 |
| RA duration, years | 8 (4-16) | 8 (5-19) | 0.22 |
| RF or anti-CCP seropositivity, n (%) | 86 (73) | 52 (90) | 0.011 |
| Any shared epitope alleles, n (%) | 80 (68) | 43 (75) | 0.34 |
| DAS28-CRP | 3.5 (2.8-4.3) | 3.8 (3.2-4.5) | 0.12 |
| CRP, mg/L | 2.3 (1.0-7.2) | 3.5 (1.2-9.3) | 0.58 |
| IL-6, pg/mL | 3.0 (1.6-7.0) | 4.5 (2.3-9.5) | 0.029 |
| Total SHS | 6 (0-26) | 12 (2-55) | 0.074 |
| Pain (100mm VAS) | 19 (10-40) | 24 (8-47) | 0.52 |
| HAQ (0 – 3) | 0.62 (0.12-1.25) | 0.75 (0.25-1.5) | 0.083 |
| Current prednisone, n (%) | 37 (31) | 30 (52) | 0.009 |
| Current non-biologic DMARDs, n (%) | 103 (88) | 47 (81) | 0.21 |
| Methotrexate, n (%) | 81 (69) | 33 (57) | 0.13 |
| Leflunomide, n (%) | 11 (9) | 8 (14) | 0.37 |
| Current biologic DMARDs, n (%) | 48 (41) | 34 (59) | 0.028 |
| TNF inhibitors, n (%) | 46 (39) | 33 (57) | 0.028 |
| Number of failed DMARDs | 1 (0-2) | 1 (0-2) | 0.80 |
| Any PFT Abnormality (n=158), n (%) | 22 (21) | 22 (43) | 0.003 |
| Any PFT Restriction or Impaired Diff., n (%) | 12 (13) | 18 (41) | <0.001 |
| Any respiratory symptoms (n=168), n (%) | 40 (36) | 29 (52) | 0.046 |
| Number of respiratory symptoms | 0 (0-1) | 1 (0-2) | 0.017 |

TABLE 7. ASSOCIATION OF PAD3/PAD4 CROSS-REACTIVE ANTIBODIES WITH PULMONARY OUTCOMES IN RA

| OUTCOME | CRUDE β | P | ADJUSTED* β | P | ADJUSTED** β | P |
|---|---|---|---|---|---|---|
| ANY CT-ILD† | 5.39 | 0.001 | 4.37 | 0.011 | 7.22 | 0.001 |
| ANY GGO† | 2.99 | 0.042 | 3.93 | 0.034 | 3.50 | 0.043 |
| ANY R/TB/HC† | 2.63 | 0.046 | 1.13 | 0.85 | 2.10 | 0.22 |
| ANY PFT ABNORMALITY† | 0.51 | 0.30 | 0.37 | 0.15 | 0.45 | 0.25 |
| ANY PFT RESTRICTION OR IMPAIRED DIFF.† | 0.48 | 0.36 | 0.40 | 0.26 | 0.59 | 0.52 |
| ANY RESPIRATORY SYMPTOMS† | 1.81 | 0.22 | 1.74 | 0.29 | 2.15 | 0.17 |
| SQUARE ROOT CT-ILD SCORE | 0.61 | 0.004 | 0.52 | 0.022 | 0.61 | 0.002 |

*ADJUSTED FOR AGE, RA DURATION, RF, CCP2, IL-6, SHS
**ADJUSTED FOR AGE, GENDER, RF, CCP2, RA DURATION, DAS28, PREDNISONE USE, METHOTREXATE USE, CURRENT AND PAST SMOKING, AND SHS
† β COEFFICIENTS ARE ODDS RATIOS

TABLE 8. OUTCOME: ANY CT-ILD

| | CRUDE OR | P | ADJUSTED* OR | P | ADJUSTED** OR | P |
|---|---|---|---|---|---|---|
| PAD3/PAD4 NEGATIVE, NEVER SMOKER; (n=61) | REFERENT | -- | REFERENT | -- | REFERENT | -- |
| PAD3/PAD4 POSITIVE, NEVER SMOKER; (n=9) | 4.08 | 0.062 | 2.66 | 0.24 | 3.01 | 0.19 |
| PAD3/PAD4 NEGATIVE, EVER SMOKER; (n=96) | 2.93 | 0.008 | 3.18 | 0.007 | 2.08 | 0.12 |
| PAD3/PAD4 POSITIVE, EVER SMOKER; (n=96) | 45.90 | 0.001 | 45.61 | 0.001 | 61.42 | 0.001 |

FIG. 12

SEQUENCE LISTING

```
<160> NUMBER OF SEQ ID NOS: 1

<210> SEQ ID NO 1
<211> LENGTH: 14
<212> TYPE: PRT
<213> ORGANISM: Oryctolagus cuniculus

<400> SEQUENCE: 1

Phe Glu Gly Ile Lys Lys Lys Lys Gln Gln Lys Ile Lys Asn
1               5                   10
```

HUMAN AUTOANTIBODIES SPECIFIC FOR PAD3 WHICH ARE CROSS-REACTIVE WITH PAD4 AND THEIR USE IN THE DIAGNOSIS AND TREATMENT OF RHEUMATOID ARTHRITIS AND RELATED DISEASES

CROSS-REFERENCE TO RELATED APPLICATIONS

This application is a Division of U.S. patent application Ser. No. 14/071,996, filed Nov. 05, 2013, which claims the benefit of U.S. Provisional Application No. 61/722,306, filed Nov. 05, 2012, the content of each of the aforementioned applications is herein incorporated by reference in their entirety.

STATEMENT OF GOVERNMENTAL INTEREST

This invention was made with government support under grant no. T32 AR48522-06 awarded by the NIH. The government has certain rights in the invention.

INCORPORATION-BY-REFERENCE OF MATERIAL SUBMITTED ELECTRONICALLY

The instant application contains a Sequence Listing which has been submitted in ASCII format via EFS-Web and is hereby incorporated by reference in its entirety. Said ASCII copy, created on Nov. 1, 2013, is named P12072-02_ST25.txt and is 586 bytes in size.

BACKGROUND OF THE INVENTION

Rheumatoid arthritis (RA) is an auto-inflammatory disease that causes pain, swelling, stiffness, and loss of joint function. RA affects at least one percent (1%) of the U.S. population (about 2.5 million individuals). Currently, the cause of RA is unknown and while there is no cure, a certain level of control of RA can be achieved through the use of biologic drugs, physical exercise, joint protection techniques and self-management methods. Early diagnosis of RA and early, aggressive treatment can help prevent joint damage, deformity and loss of physical mobility. Confirmations of diagnoses are achieved through a combination of diagnostic tests, physical examination, x-ray evidence and imaging approaches.

Peptidyl arginine deiminases (PADs) have emerged as key participants in the pathogenesis of RA. PADs catalyze the post-translational deimination of peptidyl-arginine to citrulline in a reaction requiring calcium. Several observations highlight a central role for these enzymes including the following: (i) citrullinated proteins are hallmark targets of the autoantibody response in RA; (ii) PADs catalyze the post-translational deimination of peptidyl-arginine to citrulline; and (iii) PAD2 and PAD4 are expressed in synovial tissue from patients with RA in regions co-expressing citrullinated proteins, likely in neutrophils and monocytes.

PAD4 requires calcium for catalytic activity, and calcium activation of PAD4 displays positive cooperativity. Although in vitro citrullination assays typically use 5-10 mM calcium to achieve maximal PAD4 activation, it is not possible that such high calcium concentrations are present during PAD4 activation in vivo. Indeed, extracellular free calcium concentrations are estimated to be 0.49-0.98 mM in synovial fluid and 1.1-1.3 mM in plasma, and the maximum intracellular calcium concentration achieved by primary human cells even after stimulation with various stimuli does not exceed 100 µM. The discrepancy between the in vitro requirements and in vivo availability of calcium suggests that undiscovered binding-partners may modulate PAD4 calcium sensitivity in vivo during homeostasis and RA pathology.

Several studies have demonstrated that in addition to its role in protein citrullination, PAD4 is also a frequent antigenic target in RA. PAD4 autoantibodies are detectable prior to disease onset and are associated with more erosive RA that persists despite treatment with TNFα inhibitors. Although anti-PAD4 antibodies mark a subset of RA patients with severe disease, there is marked heterogeneity in disease severity observed amongst this group and a pathogenic role for these antibodies remains undefined.

Connective tissue disease associated with interstitial lung disease, or CT-ILD, is a lung condition that affects a small number of patients with a connective tissue disease. Examples of connective tissue diseases—also known as rheumatologic, collagen vascular or autoimmune diseases—include scleroderma, rheumatoid arthritis, Sjogren's syndrome, systemic lupus erythematosus, polymyositis, dermatomyositis and mixed connective tissue disease. Patients are often diagnosed with the connective tissue disease first and develop CT-ILD later, although in some cases, the opposite occurs. CT-ILD causes inflammation or scarring (fibrosis) of the lungs, or both. The exact cause of lung damage is unknown.

Antibodies targeting citrullinated proteins (ACPA) have been implicated in the pathogenesis of ILD in RA. Citrullinated proteins and the enzymes that catalyze citrullination, the peptidylarginine deiminases (PADs), are detected in RA-ILD lung tissue and even in the lungs of heavy smokers.

The present inventors have recently shown that peripheral blood neutrophils express PAD3 protein which is capable of citrullinating intracellular targets following cell activation with calcium and ionomycin. Due to the unexpected expression of PAD3 in neutrophils, the present inventors sought to investigate PAD3 as a potential autoantigen in RA. Such novel biomarkers would be useful in identifying patients with RA and who may have severe RA earlier in the disease progression. In addition, such biomarkers may be helpful in diagnosing RA patients who may be at risk for developing CT-ILD, or which may have undiagnosed CT-ILD and allow earlier intervening treatments.

SUMMARY OF THE INVENTION

In accordance with the present invention, the inventors' studies revealed that anti-PAD3 autoantibodies were present in 12-18% of RA patients tested, and in 0% of healthy controls. Anti-PAD3 antibodies were only detected in anti-PAD4 positive sera and were found through competition experiments to be PAD3/PAD4 cross-reactive autoantibodies (AAs). Analysis of clinical features revealed that anti-PAD3 AA positive RA patients had the most erosive joint disease when compared to anti-PAD negative patients or patients with anti-PAD4 only. PAD3 AAs strikingly enhanced enzymatic activity by decreasing the requirement for calcium in the citrullination of histone H3. The enhancement of PAD4 activity at suboptimal calcium concentrations may lead to dysregulated citrullination of proteins in the inflamed RA synovium and contribute to RA pathogenesis.

In accordance with another embodiment of the present invention, the inventors used recent findings that anti-PAD3/4 cross-reactive antibodies have been shown to lower the calcium threshold required for PAD activation, an effect potentially relevant to the pathogenesis of RA-ILD. The methods of the present invention were used to explore the association between anti-PADs and radiographic RA-ILD or CT-ILD.

In accordance with an embodiment, the present invention provides an isolated, purified human autoantibody which specifically binds PAD3 or a portion or fragment thereof.

In accordance with a further embodiment, the present invention provides a method for the diagnosis of severe rheumatoid arthritis (RA) in a subject comprising: a) obtaining a sample from a subject suspected of having severe RA; b) providing a substrate having at least a first capture probe bound thereto, wherein the capture probe comprises peptidyl arginine deiminase 3 (PAD3) protein or a portion or fragment thereof which comprises an antigen recognized by autoantibodies present in the serum of subjects suffering from RA; c) contacting the substrate having the capture probe bound thereto with the sample from the subject; d) measuring the amount of a complex of the capture probe and the autoantibodies formed by step c); e) providing a normal reference level sample; f) comparing the amount of a complex of the capture probe and the autoantibodies formed from the subject suspected of having severe RA to the amount of a complex of the capture probe and the autoantibodies formed from the normal reference level sample; and g) identifying the subject suspected of having severe RA as having severe RA when the amount of a complex of the capture probe and the autoantibodies formed from the subject suspected of having severe RA is increased compared to the amount of a complex of the capture probe and the autoantibodies formed from the normal reference level sample.

In accordance with an embodiment, the present invention provides a method for identifying a subject as having connective tissue disease associated with interstitial lung disease (CT-ILD) comprising: a) obtaining a sample from a subject having or suspected of having rheumatoid arthritis (RA); b) providing a substrate having at least a first capture probe bound thereto, wherein the at least first capture probe comprises peptidyl arginine deiminase 3 (PAD3) protein or a portion or fragment thereof which comprises an antigen recognized by autoantibodies present in the serum of subjects suffering from RA; c) contacting the substrate having the at least first probe bound thereto with the sample from the subject; d) measuring the amount of a complex of the at least first capture probe and the autoantibodies formed by step c); e) providing a normal reference level sample; f) comparing the amount of the cross-reactive complex of the at least first capture probe formed from the subject having or suspected of having severe RA to the amount of a complex of the capture probe and the autoantibodies formed from the normal reference level sample; and g) identifying the subject having or suspected of having severe RA as having CT-ILD when the amount of the complex of the at least first capture probe formed from the subject having or suspected of having severe RA is increased compared to the amount of the complex of the at least first capture probe formed from the normal reference level sample.

In accordance with another embodiment, the present invention provides a method for identifying a subject having rheumatoid arthritis (RA) as having an increased risk of connective tissue disease associated with interstitial lung disease (CT-ILD) comprising: a) obtaining a sample from a subject having or suspected of having rheumatoid arthritis (RA); b) providing a substrate having at least a first capture probe bound thereto, wherein the at least first capture probe comprises peptidyl arginine deiminase 3 (PAD3) protein or a portion or fragment thereof which comprises an antigen recognized by autoantibodies present in the serum of subjects suffering from RA; c) contacting the substrate having the at least first probe bound thereto with the sample from the subject; d) measuring the amount of a complex of the at least first capture probe and the autoantibodies formed by step c); e) providing a normal reference level sample; f) comparing the amount of the cross-reactive complex of the at least first capture probe formed from the subject having or suspected of having severe RA to the amount of a complex of the capture probe and the autoantibodies formed from the normal reference level sample; and g) identifying the subject having or suspected of having RA as having an increased risk of CT-ILD when the amount of the complex of the at least first capture probe formed from the subject having RA is increased compared to the amount of the complex of the at least first capture probe formed from the normal reference level sample.

In accordance with still another embodiment, the present invention provides a method for monitoring the clinical effectiveness of a RA treatment in a subject undergoing said treatment, the method comprising: a) obtaining a sample from a subject; b) providing a substrate having a first capture probe bound thereto, wherein the capture probe comprises peptidyl arginine deiminase 3 (PAD3) protein or a portion or fragment thereof which comprises an antigen recognized by autoantibodies (AAs) present in the serum of subjects suffering from rheumatoid arthritis; (b) contacting the substrate having the capture probe bound thereto with the sample (a) from the subject; c) detecting the formation of a complex of the capture probe and the AAs and quantifying the same; d) administering to the subject a treatment regimen for RA; e) repeating steps a) to c) above; f) comparing the quantity of AAs from the subject in c) with the quantity of AAs in step e), wherein when the quantity of AAs detected after step d) is less than in step c), an assessment that the RA treatment is being therapeutically effective is made.

(700 nM) and H3 citrullination was determined by immunoblotting. (B) H3 citrullination was quantified by densitometry and molar equivalents were calculated. The fold increase in H3 citrullination with RA45-XR or RA34-IgG over the no IgG control was determined. (C) H3 was citrullinated at 0.2 mM calcium in the presence of 6 XR-IgG or 6 P4 only-IgG. (D) Citrullination was quantified by densitometry and the median citrullination between the two groups was significantly different, p=0.004. (E) Anti-PAD3 antibodies were depleted on ELISA plates coated with rPAD3 or PBS prior to use in H3 citrullination assays. H3 citrullination and equal PAD4 and IgG loading were determined by immunoblotting. (F) Specificity of the anti-PAD3 depletion was confirmed by performing immunoprecipitations with IVTT PAD4 or IVTT PAD3.

Figure 4:
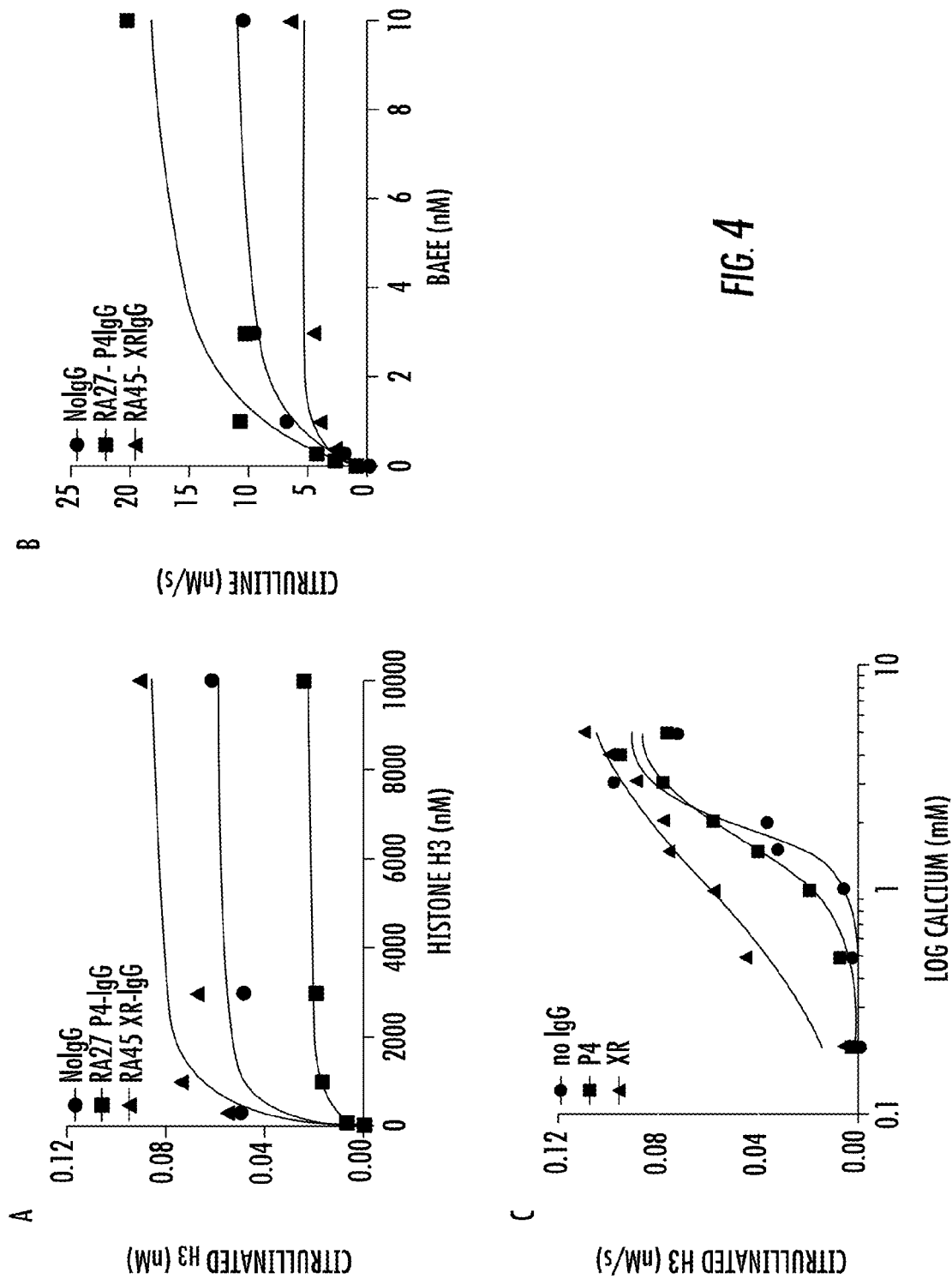

FIG. 4 depicts the PAD3 cross-reactive antibodies decrease the calcium-binding cooperativity of PAD4. PAD4 was pre-incubated at 4° C. for 45 minutes with no antibody; control IgG, anti-PAD4 only (P4) IgG, or PAD3/PAD4 cross-reactive (XR) IgG prior to use in citrullination assays. (A) Histone H3 titrations were performed at 5 mM calcium and citrullinated H3 was detected by immunoblotting. (B) BAEE titrations were performed at 2 mM calcium and citrullination was calculated using an L-citrulline standard curve. The data were fit to the Michaelis-Menten equation. (C) Calcium titrations were performed, the rate of H3 citrullination was plotted vs. calcium concentration, and data were fit to the Hill equation. Representative data from two experiments P4-IgG (RA27 and RA34), XR-IgG (RA45 and RA16), and no IgG is compiled and shown.

Figure 5:
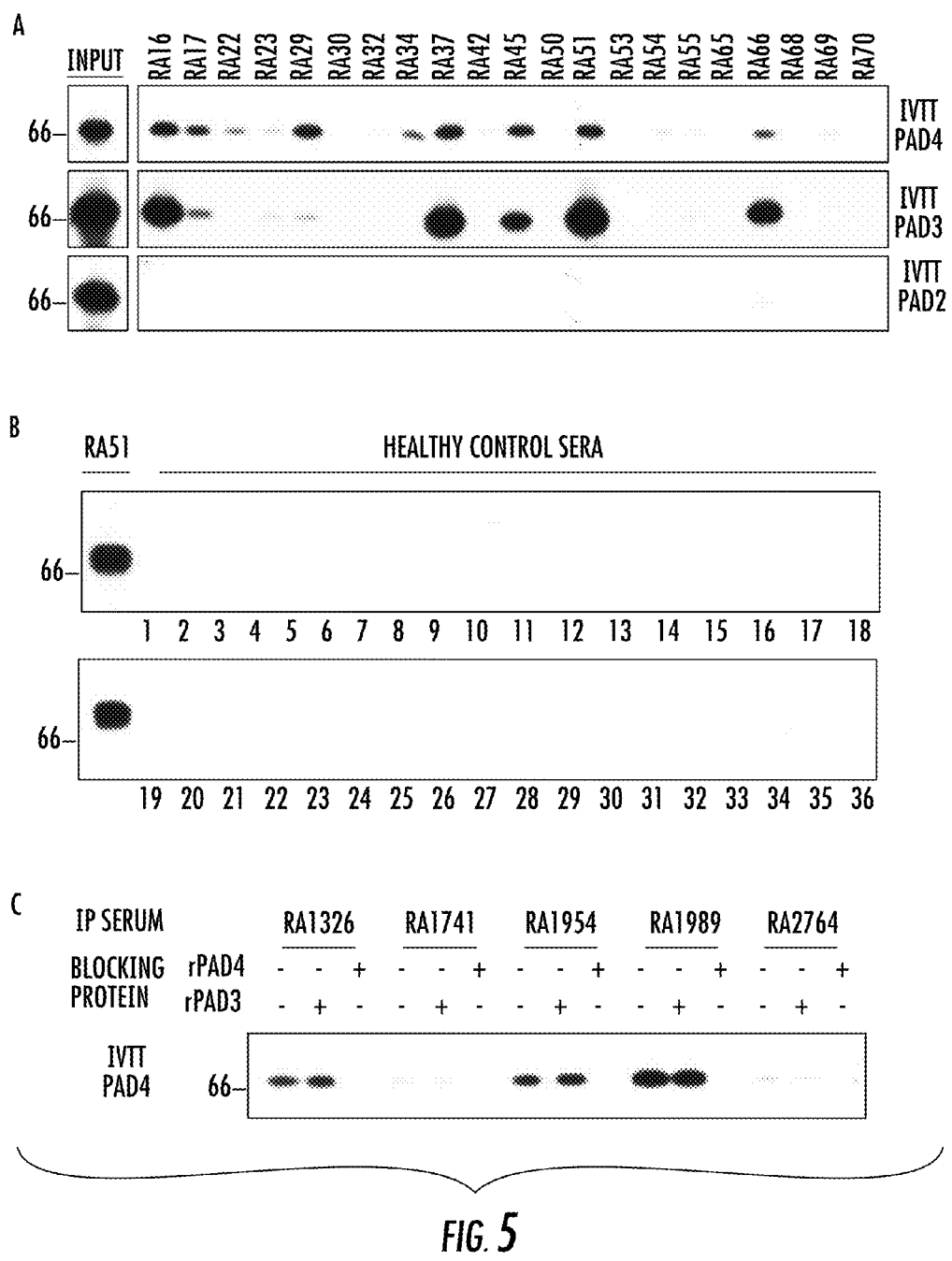

FIG. 5 shows RA convenience sera immunoprecipitations. Sera from a RA convenience cohort were used to immunoprecipitate IVTT PAD4, PAD3, or PAD2. Representative data is shown for 21 out of 44 sera.

Figure 6:
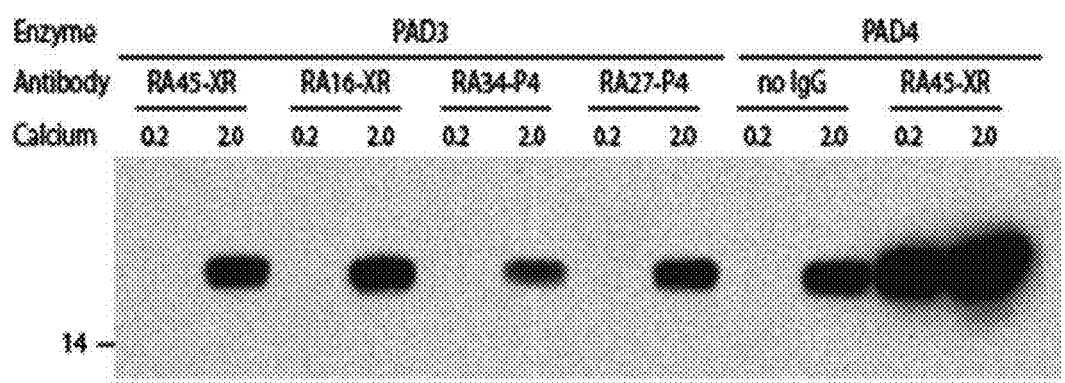

FIG. 6 reveals that PAD3 cross-reactive antibodies do not enhance PAD3 catalysis of H3. rPAD3 or rPAD4 was pre-incubated with antibodies then added to histone H3 in the presence of 0.2 or 2.0 mM calcium and 1 uM DTT. Citrullination was visualized by immunoblotting with an anti-citrullinated H3 antibody.

Figure 7:
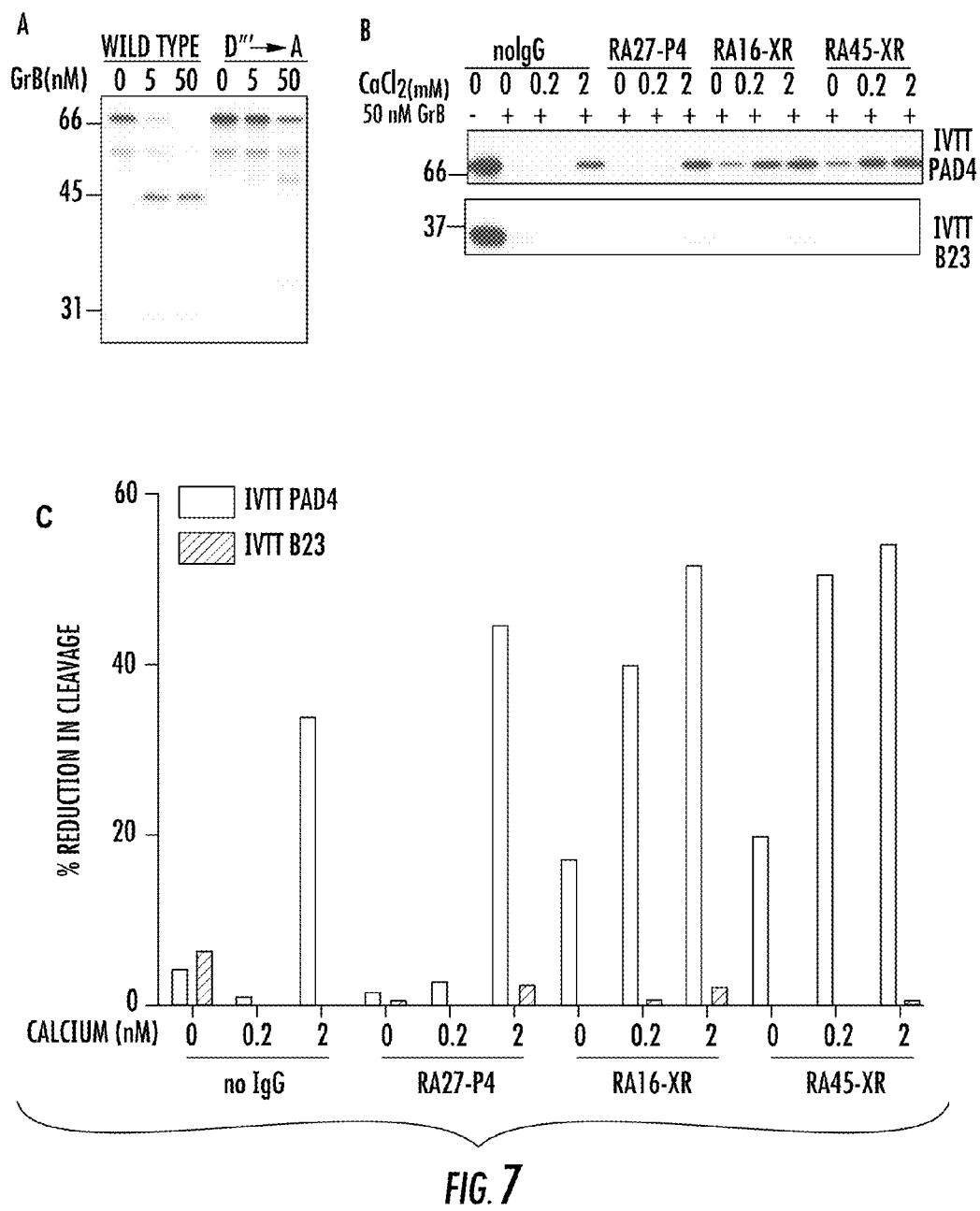

FIG. 7 shows that PAD3 cross-reactive antibodies protect PAD4 from proteolysis by granzyme B. (A) IVTT wild type or D388→A mutated PAD4 was incubated with 0, 5, or 50 nM GrB for 1 hour at 37° C. (B) IVTT PAD4 or the negative control IVTT B23 was pre-incubated with buffer alone, PAD4-only IgG (P4), or cross-reactive IgG (XR) for 1 hour at 4° C. in the presence 0, 0.2, or 2 mM calcium. Granzyme B was then added to a final concentration of 50 nM and incubated for an additional hour at 37° C. (C) Proteins were visualized by radiography and "% Reduction in cleavage" was determined by densitometry.

Figure 8:
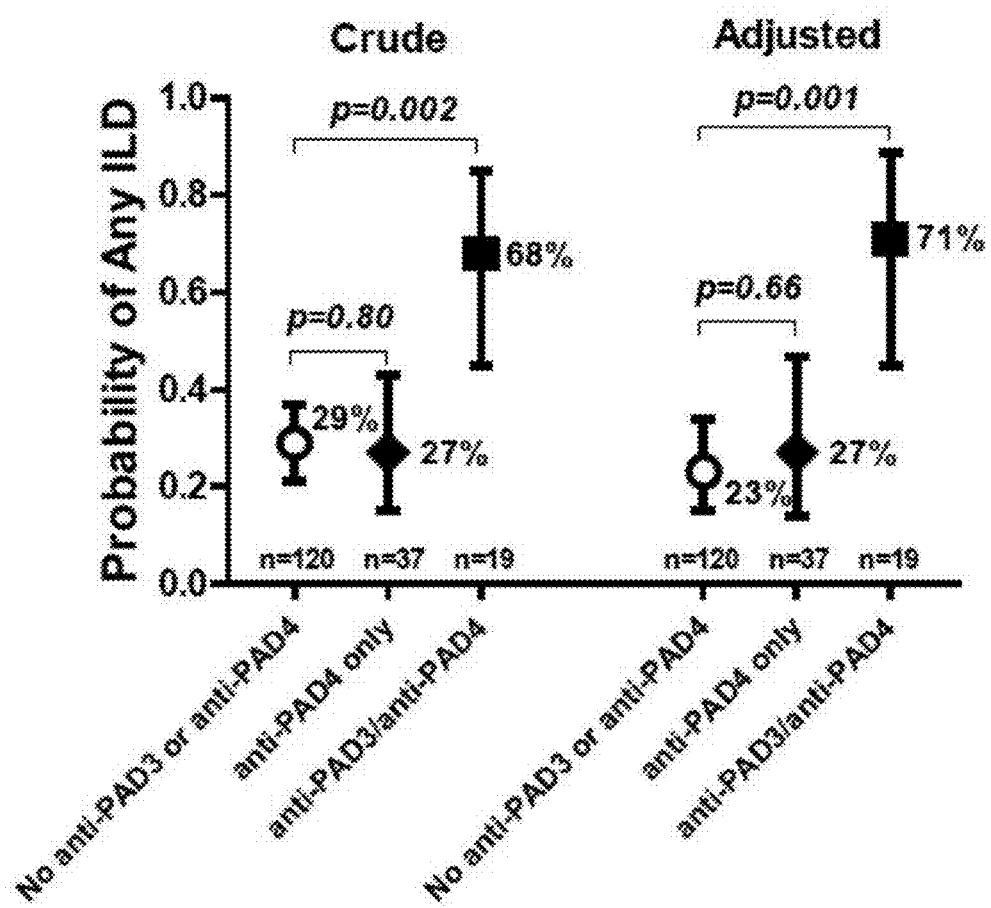

FIG. 8 shows that PAD3/PAD4 antibodies are associated with CT-ILD. The cohort was grouped based on the presence of anti-PAD3/PAD4 antibodies (closed square), anti-PAD4 antibodies only (closed diamond), or neither reactivity (open circle). The prevalence of any CT-ILD was more than double among those with anti-PAD3/PAD4 antibodies compared with those with anti-PAD4 alone or those with neither reactivity in both crude (left) and adjusted (right) analyses. Average probabilities and 95% confidence intervals are depicted. Associations adjusted for age, gender, current and past smoking, rheumatoid factor and CCP2 seropositivity, DAS28, current use of methotrexate and prednisone, RA duration, and total Sharp-van der Heijde Score.

Figure 9:
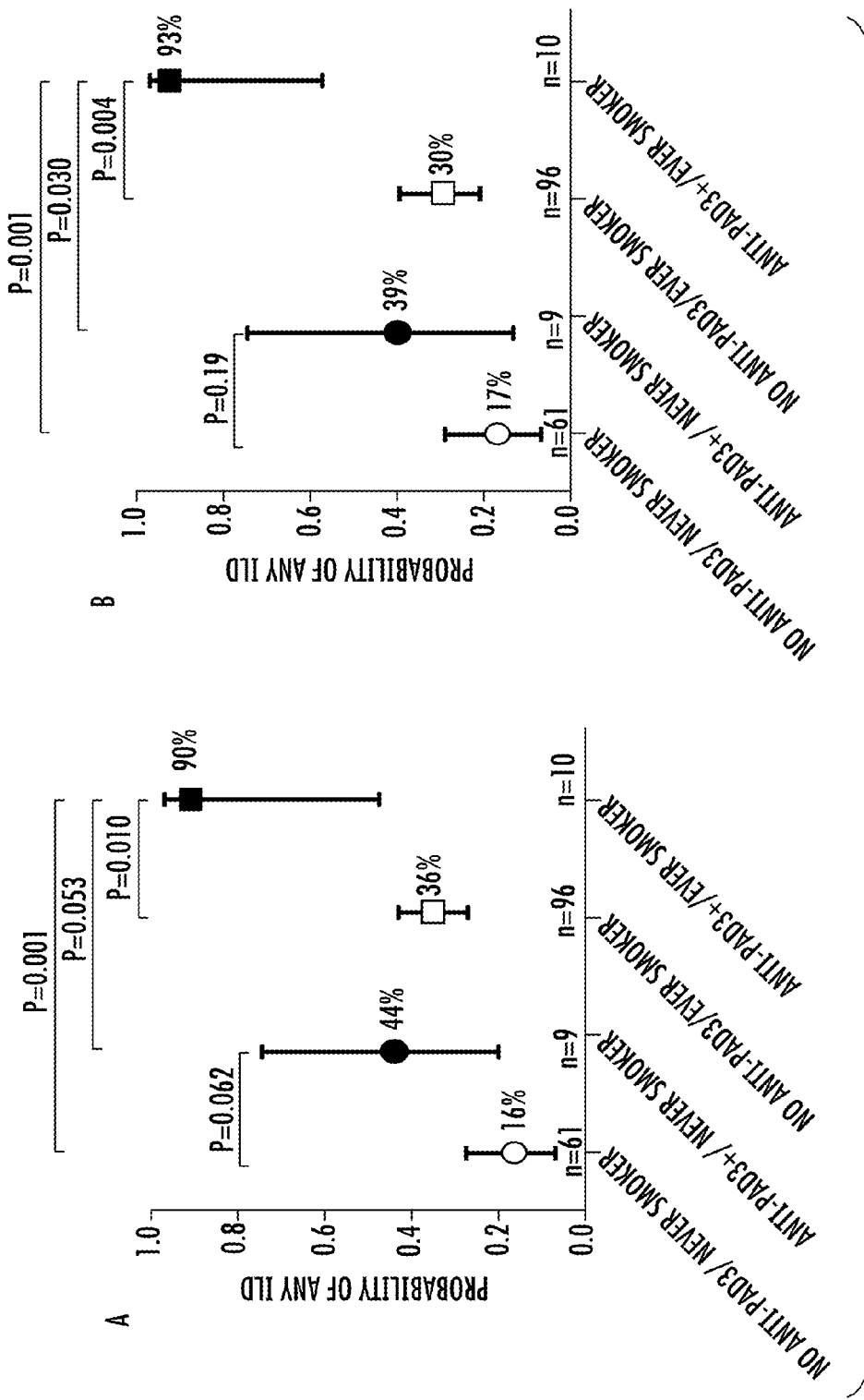

FIG. 9 depicts the combined effects of anti-PAD3/Pad4 antibodies and smoking are robust indicators of CT-ILD. The cohort was grouped based on the presence of anti-PAD3/PAD4 antibodies (closed markers) and history of ever smoking (i.e. current or former smokers). The association of anti-PAD3/PAD4 antibodies with CT-ILD was stronger among ever smokers compared to never smokers in both crude (Panel A) and adjusted (Panel B) analyses. Average probabilities and 95% confidence intervals are depicted. Panel B associations adjusted for age, gender, rheumatoid factor and CCP2 seropositivity, DAS28, current use of methotrexate and prednisone, RA duration, and total Sharp-van der Heijde Score.

FIG. 10 shows a table of patient characteristics according to PAD3/PAD4 antibody status (Table 5).

FIG. 11 shows a table of Patient Characteristics According to the Presence of CT-ILD Features (Table 6).

FIG. 12 shows a table of associations of PAD3/PAD4 cross-reactive antibodies with pulmonary outcomes in RA (Table 7), and a table of outcomes for any CT-ILD (Table 8).

DETAILED DESCRIPTION OF THE INVENTION

Disease-associated marker proteins may be found both in the tissues and in the bodily fluids of an individual who suffers from a disease or medical condition. Their levels are very low at the early stages of the disease process and increase during progression of the disease. AAs produced by patients suffering from certain diseases specifically recognize disease-associated marker proteins. The detection of AAs produced by patients with disease may therefore be used to design alternative, more reliable and sensitive tests to detect the disease condition in an individual from the very beginning of their occurrence. In particular, AAs that recognize PAD3 have been identified in patients suffering from rheumatoid arthritis.

In one or more embodiments, the present invention provides a novel biomarker which provides a link between a distinct clinical phenotype and a biochemical effect of an autoantibody on an enzyme implicated in disease pathogenesis. While the invention does not address the mechanism by which increased protein citrullination may lead to more severe disease, many of the components of the following model have been established: (i) soluble PAD2, PAD4, and citrullinated autoantigens are detected in RA synovial fluid, suggesting that PADs are released from cells undergoing apoptosis or NETosis; (ii) immune complexes and anti-PAD4 AAs have been detected in RA synovial fluid; and (iii) PAD3 autoantibodies lower the enzymatic requirement for calcium to a range known to be present in synovial fluid (0.49-0.98 mM). The PAD3 cross-reactive AAs of the present invention may therefore contribute to disease propagation by binding to soluble PAD4 and increasing the generation of citrullinated proteins in the RA joint.

As used herein, the term "antigen" refers to a substance that prompts the generation of antibodies and can cause an immune response. Examples of antigens include, but are not limited to, PAD3 and/or PAD4 that are immunologically reactive or cross-reactive with AAs present in the serum of RA patients.

As used herein, the term "antibody" means a polypeptide comprising a framework region from an immunoglobulin gene or fragments thereof that specifically binds and recognizes an antigen. Use of the term antibody is meant to include whole antibodies, including single-chain whole antibodies, antibody fragments such as Fab fragments, and other antigen-binding fragments thereof. The term "antibody" includes bispecific antibodies and multispecific antibodies so long as they exhibit the desired biological activity or function.

An "autoantibody" (abbreviated "AA") is an antibody produced by the immune system of a subject that is directed against one or more of the subject's own proteins, specifically to PAD3 and/or PAD4.

As used herein, the term "capture probe" refers to a molecule capable of binding to a target analyte, e.g., a disease-associated AA. One example of a capture probe includes antigens that recognize AAs present in a biological sample from patients having or suspected of having a disease, e.g., RA In accordance with an embodiment, the present invention provides an isolated, purified human antibody which specifically binds PAD3 or a portion or fragment thereof.

The invention provides an isolated or purified human autoantibody (AA) having antigenic specificity for PAD3 or a portion or fragment thereof.

The phrase "having antigenic specificity" as used herein means that the AA can specifically bind to and immunologically recognize the PAD3 antigens or a portion or fragment thereof.

In accordance with a further embodiment, the present invention provides a method for the diagnosis of severe rheumatoid arthritis (RA) in a subject comprising: a) obtaining a sample from a subject suspected of having severe RA; b) providing a substrate having a first capture probe bound thereto, wherein the capture probe comprises peptidyl arginine deiminase 3 (PAD3) protein or a portion or fragment thereof which comprises an antigen recognized by autoantibodies present in the serum of subjects suffering from RA; c) contacting the substrate having the capture probe bound thereto with the sample from the subject; d) measuring the amount of a complex of the capture probe and the autoantibodies formed by step c); e) providing a normal reference level sample; f) comparing the amount of a complex of the capture probe and the autoantibodies formed from the subject suspected of having severe RA to the amount of a complex of the capture probe and the autoantibodies formed from the normal reference level sample; and g) identifying the subject suspected of having severe RA as having severe RA when the amount of a complex of the capture probe and the autoantibodies formed from the subject suspected of having severe RA is increased compared to the amount of a complex of the capture probe and the autoantibodies formed from the normal reference level sample.

In accordance with another embodiment, the method described above can identify AAs cross reactive to PAD3 and PAD4, wherein step (b) further comprises a second capture probe comprising peptidyl arginine deiminase 4 (PAD4) protein or a portion or fragment thereof which comprises an antigen recognized by autoantibodies present in the serum of subjects suffering from RA; step (d) further comprises detecting the formation of a complex of the first and second capture probes and the autoantibodies; step (f) further comprises comparing the amount of the cross-reactive complex of both capture probes formed from the subject suspected of having severe RA to the amount of a complex of the capture probe and the autoantibodies formed from the normal reference level sample; and step (g) further comprises identifying the subject suspected of having severe RA as having severe RA when the amount of the cross-reactive complex of both first and second capture probes formed from the subject suspected of having severe RA is increased compared to the amount of the cross-reactive complex of both first and second capture probes formed from the normal reference level sample.

It will be understood by those of ordinary skill in the art that the inventive methods described above can include capture probes for one or more additional antibodies to other proteins of interest. For example, the inventive methods can also include capture probes for other antibodies, including autoantibodies to PAD4 protein.

Also provided by the invention is an isolated or purified polypeptide comprising a functional portion of any of the AAs described herein. The term "polypeptide" as used herein includes oligopeptides and refers to a single chain of amino acids connected by one or more peptide bonds.

As used herein, the term "reference level" is intended to mean a control level of a biomarker, e.g., disease-associated AA, used to evaluate a test level of the biomarker in a sample from an individual. A reference level can be a normal reference level in a sample from a normal subject or a disease reference level from a disease-state subject. A normal reference level is an amount of expression of a biomarker in a non-diseased subject or subjects. A disease-state reference level is an amount of expression of a biomarker in a subject with a positive diagnosis for the disease or condition. A reference level also can be a stage-specific reference level. A stage-specific reference level refers to a level of a biomarker characteristic of a given stage of progression of a disease or condition.

With respect to the inventive polypeptides, the functional portion can be any portion comprising contiguous amino acids of the AA of which it is a part, provided that the functional portion specifically binds to the PAD3 antigens.

The functional portion can comprise additional amino acids at the amino or carboxy terminus of the portion, or at both termini, which additional amino acids are not found in the amino acid sequence of the parent AA. Desirably, the additional amino acids do not interfere with the biological function of the functional portion, e.g., specifically binding to a PAD3 antigen.

The invention further provides an isolated or purified protein comprising at least one of the polypeptides described herein. By "protein" is meant a molecule comprising one or more polypeptide chains.

The AAs, polypeptides, and proteins of the invention (including functional portions and functional variants) can be glycosylated, amidated, carboxylated, phosphorylated, esterified, N-acylated, cyclized via, e.g., a disulfide bridge, or converted into an acid addition salt and/or optionally dimerized or polymerized, or conjugated.

When the AAs, polypeptides, and proteins of the invention (including functional portions and functional variants) are in the form of a salt, preferably, the polypeptides are in the form of a pharmaceutically acceptable salt. Suitable pharmaceutically acceptable acid addition salts include those derived from mineral acids, such as hydrochloric, hydrobromic, phosphoric, metaphosphoric, nitric, and sulphuric acids, and organic acids, such as tartaric, acetic, citric, malic, lactic, fumaric, benzoic, glycolic, gluconic, succinic, and arylsulphonic acids, for example, p-toluenesulphonic acid.

The AAs, polypeptides, and/or proteins of the invention (including functional portions and functional variants thereof) can be obtained by methods known in the art. Suitable methods of de novo synthesizing polypeptides and proteins are described in references, such as Chan et al., *Fmoc Solid Phase Peptide Synthesis*, Oxford University Press, Oxford, United Kingdom, 2005; *Peptide and Protein Drug Analysis*, ed. Reid, R., Marcel Dekker, Inc., 2000; *Epitope Mapping*, ed. Westwood et al., Oxford University Press, Oxford, United Kingdom, 2000; and U.S. Pat. No. 5,449,752. Also, polypeptides and proteins can be recombinantly produced using the nucleic acids described herein using standard recombinant methods. See, for instance, Sambrook et al., *Molecular Cloning: A Laboratory Manual*, $3^{rd}$ ed., Cold Spring Harbor Press, Cold Spring Harbor, N.Y. 2001; and Ausubel et al., *Current Protocols in Molecular Biology*, Greene Publishing Associates and John Wiley & Sons, NY, 1994. Further, some of the AAs, polypeptides, and proteins of the invention (including functional portions and functional variants thereof) can be isolated and/or purified from a source, such as a plant, a bacterium, an insect, a mammal, e.g., a rat, a human, etc. Methods of isolation and purification are well-known in the art. Alternatively, the AAs, polypeptides, and/or proteins described herein (including functional portions and functional variants thereof) can be commercially synthesized by companies, such as Synpep (Dublin, Calif.), Peptide Technologies Corp. (Gaithersburg, Md.), and Multiple Peptide Systems (San Diego, Calif.). In this respect, the inventive AAs, polypeptides, and proteins can be synthetic, recombinant, isolated, and/or purified.

The invention further provides an antibody, or antigen binding portion thereof, which specifically binds to a functional portion of any of the AAs described herein.

The antibody can be any type of immunoglobulin that is known in the art. For instance, the antibody can be of any isotype, e.g., IgA, IgD, IgE, IgG, IgM, etc. The antibody can be monoclonal or polyclonal. The antibody can be a naturally-occurring antibody, e.g., an antibody isolated and/or purified from a mammal, e.g., mouse, rabbit, goat, horse, chicken, hamster, human, etc. Alternatively, the antibody can be a genetically-engineered antibody, e.g., a humanized antibody or a chimeric antibody. The antibody can be in monomeric or polymeric form. Also, the antibody can have any level of affinity or avidity for the functional portion of the inventive AA. Desirably, the antibody is specific for the functional portion of the inventive AA, such that there is minimal cross-reaction with other peptides or proteins.

Methods of testing antibodies for the ability to bind to any functional portion of the inventive AA are known in the art and include any antibody-antigen binding assay, such as, for example, radioimmunoassay (RIA), ELISA, Western blot, immunoprecipitation, and competitive inhibition assays (see, e.g., Janeway et al., infra, and U.S. Patent Application Publication No. 2002/0197266 A1).

Suitable methods of making antibodies to the AAs of the present invention are known in the art. For instance, standard hybridoma methods are described in, e.g., Köhler and Milstein, Eur. J. Immunol., 5, 511-519 (1976), Harlow and Lane (eds.), Antibodies: A Laboratory Manual, CSH Press (1988), and C. A. Janeway et al. (eds), Immunobiology, 5th Ed., Garland Publishing, New York, N.Y. (2001)). Alternatively, other methods, such as EBV-hybridoma methods (Haskard and Archer, J. Immunol. Methods, 74(2), 361-67 (1984), and Roder et al., Methods Enzymol., 121, 140-67 (1986)), and bacteriophage vector expression systems (see, e.g., Huse et al., Science, 246, 1275-81 (1989)) are known in the art. Further, methods of producing antibodies in non-human animals are described in, e.g., U.S. Pat. Nos. 5,545,806, 5,569,825, and 5,714,352, and U.S. Patent Application Publication No. 2002/0197266 A1).

Phage display furthermore can be used to generate the antibody of the invention. In this regard, phage libraries encoding antigen-binding variable (V) domains of antibodies can be generated using standard molecular biology and recombinant DNA techniques (see, e.g., Sambrook et al. (eds.), Molecular Cloning, A Laboratory Manual, 3rd Edition, Cold Spring Harbor Laboratory Press, New York (2001)). Phage encoding a variable region with the desired specificity are selected for specific binding to the desired antigen, and a complete or partial antibody is reconstituted comprising the selected variable domain. Nucleic acid sequences encoding the reconstituted antibody are introduced into a suitable cell line, such as a myeloma cell used for hybridoma production, such that antibodies having the characteristics of monoclonal antibodies are secreted by the cell (see, e.g., Janeway et al., supra, Huse et al., supra, and U.S. Pat. No. 6,265,150).

Antibodies can be produced by transgenic mice that are transgenic for specific heavy and light chain immunoglobulin genes. Such methods are known in the art and described in, for example U.S. Pat. Nos. 5,545,806 and 5,569,825, and Janeway et al., supra.

Methods for generating humanized antibodies are well known in the art and are described in detail in, for example, Janeway et al., supra, U.S. Pat. Nos. 5,225,539, 5,585,089 and 5,693,761, European Patent No. 0239400 B1, and United Kingdom Patent No. 2188638. Humanized antibodies can also be generated using the antibody resurfacing technology described in U.S. Pat. No. 5,639,641 and Pedersen et al., J. Mol. Biol., 235, 959-973 (1994).

The invention also provides antigen binding portions of any of the antibodies described herein. The antigen binding portion can be any portion that has at least one antigen binding site, such as Fab, F(ab')2, dsFv, sFv, diabodies, and triabodies.

A single-chain variable region fragment (sFv) antibody fragment, which consists of a truncated Fab fragment comprising the variable (V) domain of an antibody heavy chain linked to a V domain of a light antibody chain via a synthetic peptide, can be generated using routine recombinant DNA technology techniques (see, e.g., Janeway et al., supra). Similarly, disulfide-stabilized variable region fragments (dsFv) can be prepared by recombinant DNA technology (see, e.g., Reiter et al., Protein Engineering, 7, 697-704 (1994)). Antibody fragments of the invention, however, are not limited to these exemplary types of antibody fragments.

Also, the antibody, or antigen binding portion thereof, can be modified to comprise a detectable label, such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

The inventive AAs, polypeptides, proteins, (including functional portions and functional variants thereof), nucleic acids, recombinant expression vectors, host cells (including populations thereof), and antibodies (including antigen binding portions thereof), can be isolated and/or purified. The term "isolated" as used herein means having been removed from its natural environment. The term "purified" as used herein means having been increased in purity, wherein "purity" is a relative term, and not to be necessarily construed as absolute purity. For example, the purity can be at least about 50%, can be greater than 60%, 70% or 80%, or can be 100%.

As used herein, the term "sample" means sample material derived from or contacted by living cells. The term "sample" is intended to include tissues, cells and biological fluids isolated from a subject, as well as tissues, cells and fluids present within a subject. Biological samples include, e.g., but are not limited to, whole blood, plasma, serum, semen, cell lysates, saliva, tears, urine, fecal material, sweat, buccal, skin, cerebrospinal fluid, and hair. Biological samples can also be obtained from biopsies of internal organs. Biological samples can be obtained from subjects for diagnosis or research or can be obtained from undiseased individuals, as controls or for basic research.

As used herein, the term "substrate" refers to any surface capable of having capture probes bound thereto. Such surfaces include, but are not limited to, glass, metal, plastic, or materials coated with a functional group designed for binding of capture probes or analytes. Substrates also may be referred to as slides.

As used herein, the terms "treating," "treatment," or "alleviation" refers to both therapeutic treatment and prophylactic or preventative measures, wherein the object is to prevent or slow down (lessen) the targeted pathologic condition or disorder. A subject is successfully "treated" for a disorder characterized by increased AA levels if the subject shows observable and/or measurable reduction in or absence of one or more signs and symptoms of a particular disease or condition.

In accordance with an embodiment, the present invention provides a method for identifying a subject as having connective tissue disease associated with interstitial lung disease (CT-ILD) comprising: a) obtaining a sample from a subject having or suspected of having rheumatoid arthritis (RA); b) providing a substrate having at least a first capture probe bound thereto, wherein the first capture probe comprises peptidyl arginine deiminase 3 (PAD3) protein or a portion or fragment thereof which comprises an antigen recognized by autoantibodies present in the serum of subjects suffering from RA; c) contacting the substrate having the at least first capture probe bound thereto with the sample from the subject; d) measuring the amount of a complex of the at least first capture probe and the autoantibodies formed by step c); e) providing a normal reference level sample; f) comparing the amount of the complex of the at least first capture probe formed from the subject having or suspected of having severe RA to the amount of a complex of the capture probe and the autoantibodies formed from the normal reference level sample; and g) identifying the subject having or suspected of having severe RA as having CT-ILD when the amount of the complex of the at least first capture probe formed from the subject having or suspected of having severe RA is increased compared to the amount of the complex of the at least first capture probe formed from the normal reference level sample.

In accordance with another embodiment, the present invention provides a method for identifying a subject having rheumatoid arthritis (RA) as having an increased risk of connective tissue disease associated with interstitial lung disease (CT-ILD) comprising: a) obtaining a sample from a subject having RA; b) providing a substrate having at least a first capture probe bound thereto, wherein the first capture probe comprises peptidyl arginine deiminase 3 (PAD3) protein or a portion or fragment thereof which comprises an antigen recognized by autoantibodies present in the serum of subjects suffering from RA; c) contacting the substrate having the at least first capture probe bound thereto with the sample from the subject; d) measuring the amount of a complex of the at least first capture probe and the autoantibodies formed by step c); e) providing a normal reference level sample; f) comparing the amount of the complex of the at least first capture probe formed from the subject having RA to the amount of a complex of the capture probe and the autoantibodies formed from the normal reference level sample; and g) identifying the subject having or suspected of having RA as having an increased risk of CT-ILD when the amount of the complex of the at least first capture probe formed from the subject having RA is increased compared to the amount of the complex of the at least first capture probe formed from the normal reference level sample.

It will be understood by those of ordinary skill in the art that the inventive methods described above can include capture probes for one or more additional antibodies to other proteins of interest. For example, the inventive methods can also include capture probes for antibodies, including autoantibodies to PAD4 protein.

As used herein, the terms "rheumatoid arthritis-interstitial lung disease (RA-ILD)" and connective tissue-interstitial lung disease (CT-ILD)" are used interchangeably.

As used herein, the term "multidetector computed tomography" (MDCT) is a form of computed tomography (CT) technology for diagnostic imaging. In MDCT, a two-dimensional array of detector elements replaces the linear array of detector elements used in typical conventional and helical CT scanners. The two-dimensional detector array permits CT scanners to acquire multiple slices or sections simultaneously and greatly increase the speed of CT image acquisition. The development of MDCT has resulted in the development of high resolution CT applications such as CT angiography and CT colonoscopy.

Comparing Levels of Disease-Associated AAs. The process of comparing a measured value and a reference value can be carried out in any convenient manner appropriate to the type of measured value and reference value for the disease-associated antigen or AA at issue. Measuring can be performed using quantitative or qualitative measurement techniques, and the mode of comparing a measured value and a reference value can vary depending on the measurement technology employed. For example, when a qualitative assay is used to measure disease-associated antigen or AA levels, the levels may be compared by comparing data from densitometric or spectrometric measurements (e.g., comparing numerical data or graphical data, such as bar charts, derived from the measuring device). However, it is expected that the measured values used in the methods of the invention will most commonly be quantitative values (e.g., quantitative measurements of signal intensity).

A measured value is generally considered to be substantially equal to or greater than a reference value if it is at least 95% of the value of the reference value (e.g., a measured value of 1.71 would be considered substantially equal to a reference value of 1.80). A measured value is considered less than a reference value if the measured value is less than 95% of the reference value (e.g., a measured value of 1.7 would be considered less than a reference value of 1.80). A measured value is considered more than a reference value if the measured value is at least more than 5% greater than the reference value (e.g., a measured value of 1.89 would be considered more than a reference value of 1.80).

In accordance with one or more embodiments, the examination of antibody specificity against PAD3 can be carried out, for example, in accordance with the following general immunoassay method. PAD3 protein, or a peptide or functional portion thereof, is adsorbed onto a solid phase such as a polystyrene-made microplate, followed by addition of a biological sample from a subject to the plate to bring about a reaction. The method will be described in more detail as follows. First a protein, which is a specific antigen, such as PAD3, is adsorbed onto a polystyrene-made microplate. For the adsorption, sodium carbonate-sodium hydrogen carbonate buffer may be often employed as a protein adsorption buffer. Alternatively, phosphate buffer may also be employed. As to the concentration of the specific antigen, 1 to 10 μg/ml is satisfactory. However, the examination of antibody specificity against PAD3 is also possible even at a concentration as low as 0.1 μg/ml by varying the AA concentration and reaction conditions as described later. A specific antigen or solution in a sodium carbonate-sodium hydrogen carbonate buffer or the like having an optimum concentration is added onto a polystyrene-made microplate in a predetermined amount, and allowed to stand for a predetermined period of time. Most generally, the antigen solution is allowed to stand overnight at 4° C., but may be allowed to stand at room temperature for about 2 hours, or at 37° C. for about 1 hour. The thus antigen-sensitized microplate is washed with, e.g., a phosphate buffer containing a surfactant, and an aliquot of a biological sample of a subject suspected of having AA to PAD3 is applied to the plate and allowed to react with the antigen for a predetermined time. The polystyrene-made microplate is washed again with the above-mentioned phosphate buffer, followed by addition of an enzyme-labeled anti-mouse immunoglobulin (Ig) antibody diluted to a predetermined dilution rate, thereby to cause an antigen-antibody reaction on the polystyrene-made microplate. Further, the polystyrene-made microplate is washed again in substantially the same manner as described above and subjected to measurement of enzyme activity. On the other hand, substantially the same procedures as mentioned above are repeated to determine enzyme activity except that a human plasma protein other than PAD3, which is a control antigen, such as a purified human IgG is used instead of the PAD3 that is a specific antigen. An antibody which exhibits enzyme activity when the above-mentioned specific antigen is used, but does not exhibit enzyme activity when the above-mentioned control antigen is used is a specific antibody against PAD3. In addition to the above-mentioned enzyme immunoassay method using an enzyme-labeled anti-mouse Ig antibody, the immunoassay may also be effected in substantially the same manner as mentioned above except that an anti-mouse Ig antibody labeled with a radioisotope is used and a radioactivity is measured (radio-immunoassay).

Alternatively, the examination of antibody specificity against PAD3 may also be carried out in accordance with an immunoblotting method using the plasma of a patient suffering from rheumatoid arthritis is subjected to one or two-dimensional electrophoresis without adding a protein denaturant, and the migrated protein on a electrophoresis gel is transferred onto a nitrocellulose membrane, on which the migrated protein reacts with the AA in the sample of the subject.

Beside the above, the examination of the specificity of antibody against PAD3/PAD4 may also be carried out in accordance with the other customary screening methods for detecting antibodies. For example, in the above embodiment, the substrate can have both PAD3 and PAD4 or a peptide or functional portion thereof, adsorbed onto a solid phase such as a polystyrene-made microplate, followed by addition of a biological sample from a subject to the plate to bring about a reaction. In an another embodiment, the inventive methods can include separate substrates, one having PAD3 or a peptide or functional portion thereof, adsorbed onto a solid phase, and another having PAD4 or a peptide or functional portion thereof, adsorbed onto a solid phase, and applying a portion of a sample on each.

In effecting an enzyme immunoassay using the AAs of the present invention, the anti-PAD3 antibody may be used in combination with anti-human IgG antibody or in combination with protein A. The anti-PAD3 antibody is labeled with an enzyme. Alternatively, the anti-human IgG antibody or protein A may be labeled with an enzyme. The assay is effected utilizing the antigenicity common to the PAD3 and human IgG by means of the so-called sandwich technique. Illustratively stated, the anti-anti-PAD3 antibody is adsorbed physically on a solid phase according to customary methods used in an enzyme immunoassay. As a solid phase, there may be generally employed beads made of polystyrene, glass, etc., microplates and the like. When the anti-PAD3 antibody is adsorbed on the solid phase, there may preferably be employed an anti-PAD3 antibody solution having an anti-PAD3 antibody concentration of 0.1 µg/ml or more. It is preferred that the anti-PAD3 antibody concentration be predetermined taking into consideration the sensitivity in the assay system. Preferred concentration is about 1 to 10 µg/ml. The above methods can also be performed with PAD4.

With the anti-PAD3 antibody thus adsorbed on the solid phase is reacted with serum or plasma of a subject. It is preferred that the sample be diluted with, for example, a sodium phosphate buffer containing a surfactant 10 to 100 times. The reaction was effected at 4° C. to 40° C., for 30 minutes to overnight, for example, at 4° C., overnight or at 37° C. for 30 minutes while preventing the evaporation of the reaction mixture. Then, the resulting mixture is reacted with a solution of an enzyme-labeled anti-human IgG antibody having an appropriate antibody concentration at 4° C. to 40° C. for 30 minutes to overnight. Thus, only the PAD3 in the sample is caught on the anti-PAD3 antibody adsorbed on the solid phase, and to the caught PAD3 is bonded the enzyme-labeled anti-human IgG antibody. The enzyme activity revealed by the enzyme-labeled antibody thus bonded corresponds to the amount of the caught PAD3. Accordingly, the amount of PAD3 in the sample can be determined by measuring the enzyme activity. The above methods can also be performed with PAD4.

As used herein, the term "subject" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred subject is the human.

The present invention also provides for prognostic (or predictive) assays for determining whether an individual is at risk of developing a condition, disorder or disease associated with the presence or absence of AAs. Such assays can be used for prognostic or predictive purpose, for example to thereby prophylactically treat an individual prior to the onset of a disorder characterized by or associated with AAs, e.g., anti-PAD3 antibodies. The methods described herein can also be used to determine the levels of such AAs in subjects to aid in predicting the response of such subjects to medication. Another aspect of the invention provides methods for determining an AA expression in an individual to thereby select appropriate therapeutic or prophylactic compounds for that individual.

Accordingly, the prognostic assays described herein can be used to determine whether a subject can be administered a compound (e.g., an agonist, antagonist, peptidomimetic, polypeptide, peptide, nucleic acid, small molecule, or other drug candidate) to treat a disease or condition associated with the presence of AAs. Thus, the invention provides methods for determining whether a subject can be effectively treated with a compound for a disorder or condition associated with an aberrant AA levels or in which a test sample is obtained and the AAs are detected using the assays described herein (e.g., wherein the presence, absence, and/or amount of the AAs is diagnostic for a subject that can be administered the compound to treat a disorder associated with an aberrant AA level).

The level of the AAs in a sample obtained from a subject is determined and compared with the level found in a obtained from a different subject (or population of subjects) who is free of the condition, in an earlier or later stage of the condition, has a more or less severe form of the condition or responds differently to treatments of the condition. An overabundance (or under abundance) of the AAs in the sample obtained from the subject suspected of having the condition affecting AA levels compared with the sample obtained from the different subject or population is indicative of the condition in the subject being tested.

Monitoring Clinical Efficacy. In accordance with some embodiments, the present invention provides for monitoring the influence of treatments (e.g., drugs, compounds, small molecules or devices) on the level of AAs. Such assays can also be applied in basic drug screening and in clinical trials. For example, the effectiveness of an agent to increase (or decrease) AA levels can be monitored in clinical trials of subjects. An agent that affects the level of AAs can be identified by administering the agent and observing a response. In this way, the level of the AAs can serve as a marker, indicative of the physiological response of the subject to the agent. Accordingly, this response state may be determined before, and at various points during, treatment of the individual with the agent.

In accordance with still another embodiment, the present invention provides a method for monitoring the clinical effectiveness of a RA treatment in a subject undergoing said treatment, the method comprising: a) obtaining a sample from a subject; b) providing a substrate having a first capture probe bound thereto, wherein the capture probe comprises peptidyl arginine deiminase 3 (PAD3) protein or a portion or fragment thereof which comprises an antigen recognized by autoantibodies (AAs) present in the serum of subjects suffering from rheumatoid arthritis; (b) contacting the substrate having the capture probe bound thereto with the sample (a) from the subject; c) detecting the formation of a complex of the capture probe and the AAs and quantifying the same; d) administering to the subject a treatment regimen for RA; e) repeating steps a) to c) above; f) comparing the quantity of AAs from the subject in c) with the quantity of AAs in step e), wherein when the quantity of AAs detected after step d) is less than in step c), an assessment that the RA treatment is being therapeutically effective is made.

In accordance with some other embodiments, the above method can include a modification wherein step (b) further comprises a second capture probe comprising peptidyl arginine deiminase 4 (PAD4) protein or a portion or fragment thereof which comprises an antigen recognized by autoantibodies present in the serum of subjects suffering from RA; step (c) further comprises detecting the formation of a complex of the first and second capture probes and the AAs and quantifying the same; and step (f) further comprises comparing the quantity of AAs for both the first and second capture probes from the subject in c) with the quantity of AAs in step e), wherein when the quantity of AAs detected after step d) is less than in step c), an assessment that the RA treatment is being therapeutically effective is made.

In accordance with another embodiment, the present invention provides one or more kits for diagnosis of severe rheumatoid arthritis (RA) in a subject, and/or identifying a subject having rheumatoid arthritis (RA) as having an increased risk of connective tissue disease associated with interstitial lung disease (CT-ILD), and/or monitoring the clinical effectiveness of a RA treatment in a subject. The kits comprise substrates for binding AA and PAD3 and PAD4 proteins, peptides or fragments thereof, as well as antibodies which exhibit enzyme activity when the above-mentioned specific antigens are used, but do not exhibit enzyme activity when the above-mentioned control antigen, and are specific antibodies against PAD3 and/or PAD4 Immunoassay and ELISA reagents and the like which are known to those of ordinary skill in the art can be included in these kits.

Kits according to the present invention are assemblies of reagents for testing antibody binding. They are typically in a package which contains all elements, optionally including instructions. Instructions may be in any form, including paper or digital. The instructions may be on the inside or the outside of the package. The instructions may be in the form of an internet address which provides the detailed manipulative or analytic techniques. The package may be divided so that components are not mixed until desired.

Components of the kits of the present invention may be in different physical states. For example, some components may be lyophilized and some in aqueous solution. Some may be frozen. Individual components may be separately packaged within the kit. Other useful tools for performing the methods of the invention or associated testing, therapy, or calibration may also be included in the kits, including buffers, enzymes, gels, plates, detectable labels, vessels, etc. Kits may-include tools for collecting suitable samples, such as tools for collecting oral swabs, oral biopsies, and endoscopes.

It will be understood by those of ordinary skill in the art that the inventive methods and kits described herein can be used in conjunction with other diagnostic and therapeutic methods.

The methods and kits of the present invention can be used to monitor efficacy of a therapeutic regimen, for example, whether a chemotherapeutic agent or a biological agent. Testing can also be used to determine what therapeutic or preventive regimen to employ on a patient. Moreover, testing can be used to stratify patients into groups for testing agents and determining their efficacy on various groups of patients.

In the case of a diagnosis or characterization, information comprising data or conclusions can be written or communicated electronically or orally. The identification may be assisted by a machine. Communication of the data or conclusions may be from a clinical laboratory to a clinical office, from a clinician to a patient, or from a specialist to generalist, as examples. The form of communication of data or conclusions typically may involve a tangible medium, or physical human acts. In a preferred embodiment, the methods allow a clinician or clinical laboratory to determine that a subject has for example, severe RA or an increased risk of CT-ILD, and can change the therapeutic regimen to one that is more aggressive, for example.

EXAMPLES

Rheumatoid arthritis subjects and controls. Sera were obtained from 36 healthy controls, 44 RA patients from a convenience sample, and 194 patients from the "Evaluation of Subclinical Cardiovascular Disease and its Predictors of events in Rheumatoid Arthritis" (ESCAPE RA) longitudinal cohort. In ESCAPE RA, disease activity and severity were assessed at baseline and at a final visit occurring an average of 39±4 months post-baseline. Radiographs of the hands and feet were obtained at these visits and scored according to the Sharp-van der Heijde (SvdH) method. All individuals provided informed consent as approved by the Johns Hopkins Institutional Review Board and were followed at the Johns Hopkins Arthritis Center.

Rheumatoid arthritis subjects with cardiovascular disease. RA patients participating in a study of subclinical cardiovascular disease underwent multi-detector computed tomography (MDCT) of the chest with interpretation by a pulmonary radiologist for ILD features. A semi-quantitative ILD Score (ILDS; range 0-32) was calculated. Concurrent serum samples were assessed for antibodies against PAD by immunoprecipitation of $S^{35}$-labeled PAD3 and 4.

Immunoblotting was performed using rabbit anti-PAD4 (1:5000, raised against FEGIKKKKQQKIKN (SEQ ID NO: 1)), rabbit anti-histone H3 (1:25000), rabbit anti-citrullinated H3 (1:2000, Abcam ab5103), or goat anti-human IgG (1:10000, Jackson 109-036-088).

Immunoprecipitation and blocking. cDNA encoding pCDNA3.1-PAD3 or pEFDEST51-PAD4 was in vitro transcribed and translated (IVTT) in the presence of $S^{35}$-methionine (Promega, L1170). Radiolabeled proteins were immunoprecipitated with 1 ul of serum in NP40 lysis buffer/0.2% BSA for 1 hour at 4° C. Protein A beads were added and incubated for 30 minutes at 4° C. Beads were washed and boiled in SDS sample buffer. Samples were separated by gel electrophoresis and immunoprecipitated proteins were visualized by radiography. For blocking experiments, patient serum was incubated with 0 or 300 ng of recombinant PAD3 or PAD4 at 4° C. for 30 minutes prior to use in IVTT PAD3 or PAD4 immunoprecipitations. Densitometry was performed on all films and values were normalized to a high titer anti-PAD3 serum. Antibody positivity was defined as a normalized densitometry value of >0.01 and blocking efficiency was calculated.

Depletion of anti-PAD3 antibodies by ELISA. High-binding ELISA plates were coated with 1000 ng/well of rPAD3 in PBS/0.02% azide overnight at 4° C. Plates were blocked with 3% BSA/PBS/0.02% azide for 2 hours then incubated with 5 mM EDTA/PBS at 37° C. for 1 hour to chelate free calcium. IgG was added and incubated overnight at 4° C. prior to use in citrullination assays or immunoprecipitations.

Citrullination assay. IgG from PAD3/PAD4 cross-reactive, PAD4 only, or PAD-negative sera was purified using Melon Gel columns. 1 μM IgG was incubated with 10 nM recombinant PAD4 for 45 minutes at 4° C. in 100 mM Tris-HCl pH 7.4. PAD4/IgG mixtures were mixed with 0-10 μM histone H3.1 in the presence of increasing amounts of $CaCl_2$ and incubated at 37° C. for 90-110 minutes. Proteins were boiled in SDS sample buffer, separated by electrophoresis, transferred to nitrocellulose, and immunoblotted as indicated. Molar equivalents of citrullinated H3 were calculated by normalizing to a densitometry value obtained from 1 μM H3 maximally citrullinated with 100 nM PAD4, 5 mM calcium, and DTT. Citrullination of 0-10 mM Benzoyl-Arginine Ethyl Ester (BAEE) (RDI, DR-AV009X) was performed with 50 nM PAD4 and 2 mM calcium and quantified as previously described.

Depletion of anti-PAD3 antibodies by ELISA. EIA high binding ELISA plates were coated with 1000 ng/well of recombinant PAD3 in PBS/0.02% azide overnight at 4° C. Plates were washed in PBS/0.05% Tween-20 and blocked with 3% BSA/PBS/0.02% azide for 2 hours. Plates were washed again and incubated with 5 mM EDTA/PBS at 37° C. for 1 hour to chelate free calcium. IgG was added and incubated overnight at 4° C. IgG was then removed and used for citrullination assays or immunoprecipitations.

Granzyme B cleavage assays. In order to map the GrB cleavage site, pEFDEST51-PAD4 was mutated by site directed mutagenesis (from $MGPD^{388}$ to $MGPA^{388}$). Wild-type or mutated IVTT PAD4 was incubated with 0, 5, or 50 nM recombinant human GrB for 1 hour at 37° C. in either ICE assay buffer (10 mM Hepes pH 7.4/2 mM EDTA pH 7.4/1% NP-40). For experiments with IgG, IVTT PAD4 was pre-incubated with 5 μg of IgG for 1 hour at 4° C. in the presence of 0, 0.2, or 2 mM calcium. The PAD4/IgG mixture was then incubated at 37° C. for 1 hour with 50 nM GrB in 100 mM Tris-HCL pH 7.4. GrB cleavage was visualized by radiography and cleavage was quantified by densitometry.

Calculations. Data were fit to the Michaelis-Menten or Hill equations by nonlinear regression using Prism. The Michaelis-Menten equation was expressed as $v=V_{max}*[S]/(K_m+[S])$. The Hill equation was expressed as $v=V_{max}*[Ca^{2+}]^n/(K+[ca^{2+}]^n)$, with n representing the Hill coefficient. Values for $K_{0.5}$, the calcium concentration producing half-maximal activation, were calculated from the relation $K_{0.5}=n^{th}$ root(K). Granzyme B cleavage efficiency was calculated using the equation, % substrate cleaved=$100\times(1-e^{-kcat\times[E]/Km\times time})$.

Example 1

Figure 1:
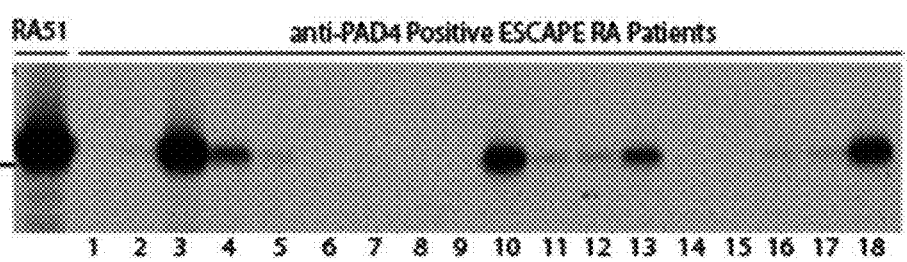
FIG. 1 shows that PAD3/PAD4 cross-reactive AAs are present in a subset of RA patients. (A) anti-PAD4 positive (upper panel), anti-PAD4 negative (lower panel) ESCAPE RA patient sera were used to immunoprecipitate IVTT PAD3 Immunoprecipitated IVTT-PAD3 was resolved on an SDS-PAGE gel and imaged by radiography. Densitometry was performed and values were normalized to a known anti-PAD3 positive serum (RA51). Representative data from 36 out of 194 RA patients is shown. (B) Anti-PAD3/anti-PAD4 positive patient sera was pre-incubated with 0 or 300 ng of rPAD3 or rPAD4 for 45 minutes at 4° C. prior to performing IVTT PAD3 or IVTT PAD4 immunoprecipitations.
Figure 1:
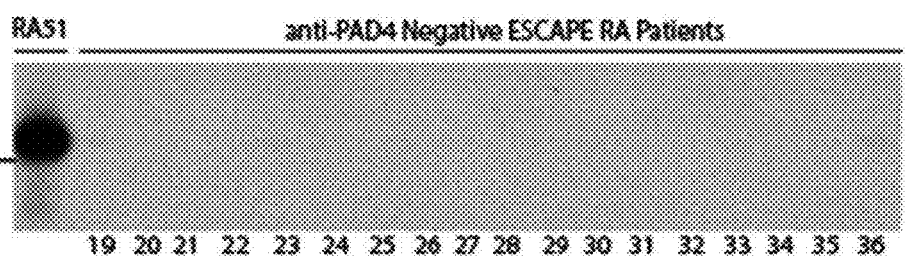
Figure 1:
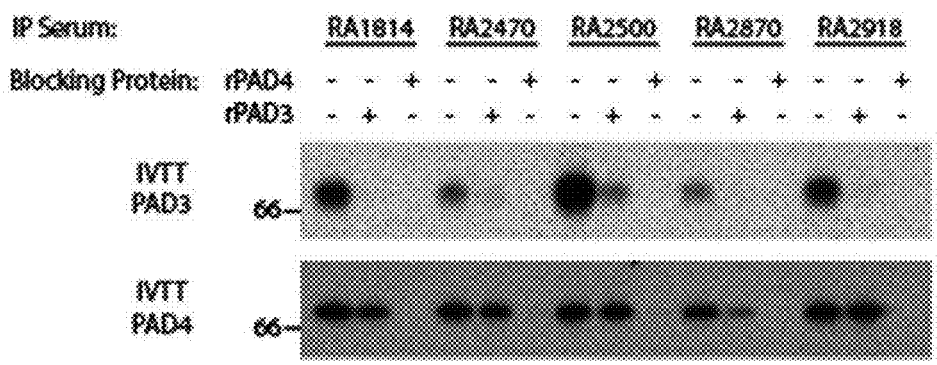

In order to screen for anti-PAD3 antibodies, sera from a convenience sample of RA patients were initially used to immunoprecipitate $^{35}$S-methionine labeled in vitro transcribed and translated (IVTT) PAD3 protein. PAD3 autoantibodies were detected in 18% (8/44) of sera. Anti-PAD3 was exclusively present in patients with PAD4 antibodies and were observed in 40% of anti-PAD4 positive sera (FIG. 5A). In order to determine the prevalence of anti-PAD3 in a large, well-defined group of established RA patients, PAD3 immunoprecipitation was performed on 194 sera from the ESCAPE RA cohort (a prospective observational cohort study of subclinical cardiovascular disease in RA, for which extensive clinical and serologic data was available). Again, anti-PAD3 was only detected in the serum of patients with anti-PAD4 antibodies (FIG. 1A, representative positives shown in lanes 3, 4, 10, 13 and 18). The overall prevalence of anti-PAD3 antibodies was 12% and these antibodies were present in 32% of anti-PAD4 positive individuals. Anti-PAD3 was not detected in serum from 36 healthy controls (FIG. 5B). Anti-PAD3 antibodies are therefore RA-specific, and are uniformly associated with anti-PAD4 antibodies.

Example 2

The uniform association of anti-PAD3 with anti-PAD4 suggested that they are either cross-reactive or distinct antibodies that are always generated together. In order to determine if the two antibodies were recognizing the same or distinct antigens, competition experiments were performed. Recognition of radiolabeled IVTT PAD3 was almost completely abrogated by pre-incubation of eight anti-PAD3 positive sera with unlabeled recombinant PAD4 (rPAD4), demonstrating that these are cross-reactive (FIG. 1B, representative data shown in upper panel). Interestingly, only a subset of the PAD4 antibody pool in a given patient's serum cross-reacted with PAD3. Thus, pre-incubation of eight cross-reactive sera with unlabeled rPAD3 reduced the immunoprecipitation of IVTT PAD4 by an average of 43% with a range of 2.2-83%, depending on the individual serum tested (FIG. 1B, representative data shown in lower panel). Pre-incubation with rPAD3 did not affect the immunoprecipitation of IVTT PAD4 by sera from anti-PAD3 negative patients (FIG. 5C). Importantly, PAD3/PAD4 cross-reactive antibodies did not recognize the homologous protein, PAD2 (FIG. 5A). These data demonstrate that a subset of RA patients have antibodies which bind to an epitope shared by PAD3 and PAD4 (we will refer to these as PAD3/PAD4 cross-reactive antibodies of the present invention).

Example 3

Figure 2:
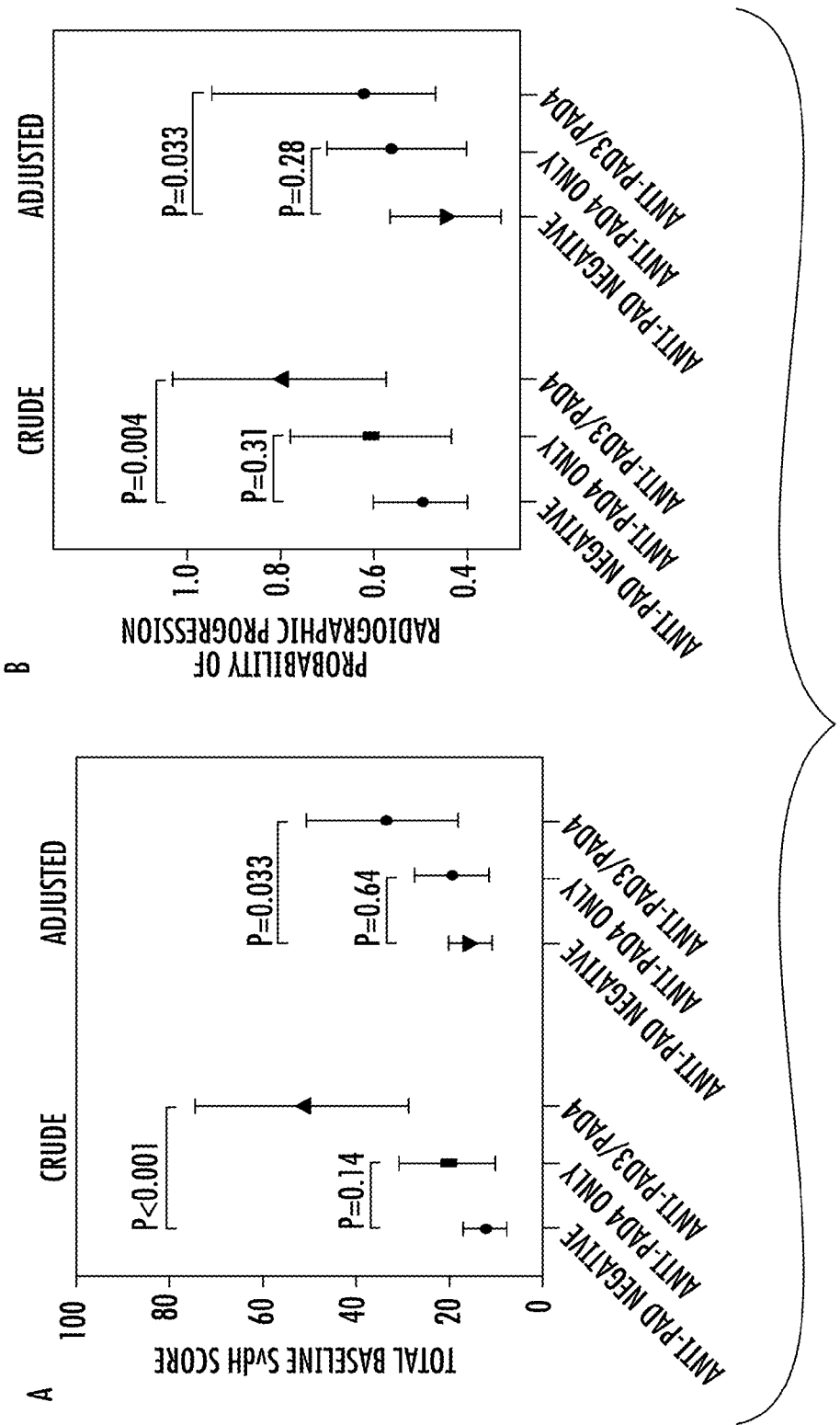
FIG. 2 illustrates that patients with PAD3 cross-reactive antibodies have the most severe progressive disease. (A) 194 patients in the ESCAPE RA cohort were divided into three groups according to their autoantibody status (Anti-PAD negative, Anti-PAD4 only, or Anti-PAD3/PAD4). The mean total baseline SvdH Score for each group was determined and revealed a significant association of PAD3/PAD4 cross-reactive antibodies with Sharp score (Crude). (B) Sharp scores were available on 150 patients at follow-up, with annualized rates of progression determined as those patients with any increase in SvdH score from baseline (Crude). These associations were maintained after adjusting for age, gender, RA duration, shared epitope alleles, anti-CCP status, and log CRP levels (Adjusted).

Cross-reactive antibodies are associated with severe erosive joint disease. Several previous studies have demonstrated that anti-PAD4 antibodies are associated with increased disease severity in RA. Due to the cross-reactivity of anti-PAD3 with PAD4, we sought to determine if this association is maintained in RA patients with anti-PAD3 antibodies and if novel associations existed. Patients from the ESCAPE RA cohort were divided into three groups based on PAD antibody status (Group 1: anti-PAD negative, Group 2: anti-PAD4 only, and Group 3: anti-PAD3/PAD4). The total Sharp van der Heidje score (SvdH) [a cumulative measure of disease severity that scores the degree of radiographic joint space narrowing and bone erosion in multiple joints of the hands, wrists, and feet] was available for all 194 patients at the baseline visit. For 150 individuals, this score was also available at follow-up, an average of 39±4 months later. Patients with anti-PAD3 antibodies had a more than 2.5-fold higher baseline SvdH score than those with anti-PAD4 only (p=0.039) and a more than 4.5-fold higher score than PAD antibody negative patients (p<0.001) (FIG. 2A and Table 1). Additionally, anti-PAD3 positive patients were significantly more likely to have radiographic progression compared to PAD antibody negative individuals (80 vs. 50%, respectively; p=0.004) despite equivalent treatment with DMARDs and glucocorticoids (FIG. 2B and Table 1). The associations of anti-PAD3 antibodies with disease severity and mean probability of progression were maintained after adjusting for cohort-specific indicators of radiographic damage (age, sex, disease duration, anti-CCP positivity, presence of shared-epitope alleles, and CRP) (FIG. 2), indicating that the anti-PAD3 positive subset is an important driver of the previously defined association of anti-PAD4 autoantibodies with erosive disease.

In addition to the association with disease severity, anti-PAD3 antibodies were associated with significantly longer RA duration compared to anti-PAD4 only (p=0.021) and PAD antibody negative groups (p<0.001) (Table 1). The association of anti-PAD3 antibodies with RA duration was independent of age at disease onset and each additional year post RA diagnosis conferred an 8% higher odds of observing anti-PAD3 antibodies (p=0.009) (Table 2). Additionally, 91% of patients with anti-PAD3 antibodies had one or more HLA-DRB1 shared epitope alleles compared to only 73% of patients with anti-PAD4 only (p=0.012) and 65% without PAD antibodies (p=0.082). Interestingly, these associations were not observed in previous studies of anti-PAD4 antibodies, again reinforcing that anti-PAD3 is marking a distinct patient subset.

TABLE 2

RA duration is independently associated with PAD3/PAD4 cross-reactive antibodies.

|  | Model 1 | | Model 2 | |
| --- | --- | --- | --- | --- |
|  | OR | p | OR | p |
| Age at RA diagnosis, per year | 0.95 | 0.016 | 1.01 | 0.63 |
| RA duration from diagnosis, per year |  |  | 1.08 | 0.009 |

Model 1 is unadjusted.
Model 2 is adjusted for RA duration and age at disease onset.

Example 4

PAD3 cross-reactive antibodies increase the sensitivity of PAD4 to $Ca^{2+}$ activation. The finding that patients with PAD3/PAD4 cross-reactive antibodies have the most severe disease suggested that these antibodies may play a pathogenic role in vivo. We hypothesized that these antibodies contribute

TABLE 1

Characteristics of ESCAPE RA patients by anti-PAD3 and anti-PAD4 status.

|  | Anti-PAD negative (P0) | anti-PAD4only (P4) | Anti-PAD3/PAD4 (XR) | XR vs. P0 | P4 vs. P0 | XR vs. P4 |
| --- | --- | --- | --- | --- | --- | --- |
| Age, years | 59 ± 8 | 58 ± 9 | 62 ± 8 | 0.26 | 0.42 | 0.14 |
| Male gender, n (%) | 43 (35) | 27 (55) | 9 (39) | 0.72 | 0.017 | 0.21 |
| Caucasian, n (%) | 102 (84) | 46 (94) | 18 (78) | 0.53 | 0.075 | 0.049 |
| BMI | 28.3 ± 5.1 | 28.6 ± 5.7 | 28.2 ± 5.7 | 0.94 | 0.75 | 0.80 |
| Ever smoking, n (%) | 80 (66) | 23 (47) | 11 (50) | 0.16 | 0.024 | 0.81 |
| Current smoking, n (%) | 19 (16) | 4 (8) | 0 (0) | 0.079 | 0.20 | 0.17 |
| RA duration, years | 7 (4-15) | 13 (6-19) | 21 (11-28) | <0.001 | 0.017 | 0.021 |
| RF seropositivity, n (%) | 75 (61) | 36 (73) | 17 (74) | 0.26 | 0.14 | 0.97 |
| Anti-CCP seropositivity, n | 77 (63) | 42 (86) | 19 (83) | 0.070 | 0.004 | 0.73 |
| Any HLA-DRB1 SE | 78 (65) | 36 (73) | 21 (91) | 0.012 | 0.29 | 0.082 |
| DAS28, median (IQR) | 3.6 (2.9-4.3) | 3.4 (2.9-4.3) | 3.8 (3.3-4.5) | 0.43 | 0.42 | 0.25 |
| Swollen joint count, | 7 (3-10) | 6 (2-11) | 8 (4-12) | 0.45 | 0.42 | 0.29 |
| Tender joint count, | 7 (3-13) | 5 (2-10) | 5 (2-13) | 0.53 | 0.21 | 0.72 |
| HAQ score (0-3), | 0.63 (0.13 - | 0.63 (0 - | 1.13 (0.13 - | 0.21 | 0.44 | 0.10 |
| CRP, median (IQR) | 2.09 (0.97 - | 3.32 (1.42 - | 2.64 (1.62 - | 0.19 | 0.12 | 0.74 |
| Sharp Score (BS), median | 30 (12-85) | 56 (21-123) | 139 (66 - | <0.001 | 0.036 | 0.039 |
| Sharp Score (vdH), | 6 (0-26) | 9 (1-60) | 49 (12-98) | <0.001 | 0.20 | 0.015 |
| Erosion score, median | 2 (0-8) | 4 (0-20) | 15 (2-38) | <0.001 | 0.082 | 0.055 |
| JSN score, median (IQR) | 3 (0-18) | 7 (0-29) | 33 (9-63) | <0.001 | 0.33 | 0.011 |
| Δ Sharp Score, median | 0.14 (0 - | 0.62 (0 - | 0.62 (0.30 - | 0.13 | 0.17 | 0.90 |
| Δ Erosion Score, median | 0 (0-0.30) | 0 (0-0.70) | 0 (0-0.64) | 0.16 | 0.10 | 0.99 |
| Δ JSN Score, median | 0 (0-1.17) | 0.52 (0 - | 0.31 (0 - | 0.51 | 0.28 | 0.79 |
| Any increase in SvdH | 49 (50) | 22 (59) | 12 (80) | 0.030 | 0.33 | 0.16 |
| Non-biologic DMARDs, n | 102 (84) | 44 (90) | 17 (74) | 0.23 | 0.35 | 0.081 |
| Biologic DMARDs, n (%) | 53 (44) | 23 (47) | 11 (48) | 0.72 | 0.71 | 0.94 |
| Glucocorticoids, n (%) | 44 (36) | 21 (43) | 9 (39) | 0.78 | 0.41 | 0.77 |

* 150 individuals had radiographs at follow-up (n = 98 in group 1; n = 37 in group 2; and n = 15 in group 3)
IQR = interquartile range
SvdH = Sharp van der Heijde Score
DMARDs = disease modifying antirheumatic drugs to disease pathogenesis by modulating PAD enzymatic function and generation of citrullinated proteins. This was explored using the well-defined physiologic PAD4 substrate, histone H3, at a range of calcium concentrations.

In the absence of antibody, PAD4 activity was maximal at 5 mM calcium and declined abruptly below 2 mM, such that activity at physiologic calcium concentrations was markedly diminished (FIG. 3A). A cross-reactive antibody (RA45) strikingly expanded the range of calcium concentrations able to support PAD4 catalytic activity, with robust histone citrullination observed over a physiologic range of calcium concentrations (0.2-1 mM calcium). In fact, this cross-reactive antibody increased the rate of histone H3 citrullination over 400-fold at 0.2 mM calcium, compared to 10.7-fold with a PAD4-only IgG (FIG. 3B).

The ability of cross-reactive antibodies to activate PAD4 at low calcium concentrations was further explored by citrullinating H3 in the presence of IgG from six cross-reactive antibody-positive and -negative individuals at 0.2 mM $Ca^{2+}$ (FIG. 3C). IgG from cross-reactive patients increased the rate of H3 citrullination by an average of 500-fold compared to that observed with PAD4-only sera, from 0.03±0.2 pM/s to 15.0±10.0 pM/s (p=0.004) (FIG. 3D). Interestingly, although cross-reactive antibodies also bind to PAD3, they did not augment citrullination of H3 by PAD3 at 0.2 mM or 2 mM calcium, indicating that the observed rate enhancement was not due to an effect on the histone substrate, but rather the PAD4 enzyme itself (FIG. 6). The increase in PAD4 activity was specifically dependent upon the PAD3/PAD4 cross-reactive IgG subset because depletion of anti-PAD3 antibodies on solid-immobilized rPAD3 reduced H3 citrullination by 92-100% (FIGS. 3E and F). Thus, PAD3/PAD4 cross-reactive antibodies increase the sensitivity of PAD4 to calcium and greatly augment histone citrullination at $Ca^{2+}$ concentrations that are relevant physiologically.

Example 5

PAD3 cross-reactive antibodies have little effect on $K_m$ and $k_{cat}$ at saturating $Ca^{2+}$. To better understand the molecular basis for the observed enhancement of PAD4 catalytic activity by cross-reactive antibodies, kinetic constants were determined for the substrates histone H3 and the small molecule benzoyl-arginine ethyl ester (BAEE). Kinetic measurements were conducted at saturating $Ca^{2+}$ concentrations in order to avoid effects arising from shifts in calcium ion sensitivity and determine if cross-reactive antibodies were directly affecting formation of the active site or affinity of PAD4 for substrate. Fits to the Michaelis-Menten equation are shown in FIGS. 4A and B. In the absence of antibody, these two substrates differ markedly in that $K_m$ (the steady-state dissociation constant) is 3700-fold lower for histone H3, while $k_{cat}$ (the rate constant for turnover of the enzyme-substrate complex) is 40-fold faster for BAEE (Table 3). Thus, the catalytic efficiency, $k_{cat}/K_m$, is almost 100-fold better for the histone substrate at saturating calcium.

TABLE 3

Kinetic parameters for substrate dose responses at saturating calcium.

| Substrate | no IgG | RA27-P4 | RA45-XR |
|---|---|---|---|
| Histone H3 | | | |
| Vmax (M/s) | $6.05 \times 10^{-11}$ | $2.36 \times 10^{-11}$ | $8.88 \times 10^{-11}$ |
| $K_m$ (M) | $2.56 \times 10^{-7}$ | $3.73 \times 10^{-7}$ | $3.44 \times 10^{-7}$ |
| $k_{cat}$ (s$^{-1}$) | $6.05 \times 10^{-3}$ | $2.36 \times 10^{-3}$ | $8.88 \times 10^{-3}$ |
| $k_{cat}/K_m$ (M$^{-1}$s$^{-1}$) | 23600 | 6330 | 25800 |
| BAEE | | | |
| $V_{max}$ (M/s) | $1.21 \times 10^{-8}$ | $2.07 \times 10^{-8}$ | $0.567 \times 10^{-8}$ |
| $K_m$ (M) | $0.96 \times 10^{-3}$ | $1.36 \times 10^{-3}$ | $0.25 \times 10^{-3}$ |
| $k_{cat}$ (s$^{-1}$) | 0.242 | 0.415 | 0.113 |
| $k_{cat}/K_m$ (M$^{-1}$s$^{-1}$) | 252 | 306 | 448 |

Remarkably, addition of cross-reactive antibodies had minimal effect on PAD4 activity at saturating calcium. Only modest rate enhancements were observed for BAEE and none of the antibodies increased the catalytic efficiency of PAD4 more than 2-fold from that observed with enzyme alone ($k_{cat}/K_m$=252 M$^{-1}$ s$^{-1}$) (FIG. 4B and Table 3). This is consistent with what has previously been observed for anti-PAD4 antibodies at 1.5 mM and 10 mM calcium. Since citrullination of BAEE does not require extended macromolecular interactions, presumably this small molecule reports on events limited to the fundamental active site. Similarly modest rate enhancements were observed when histone H3 was the substrate. The cross-reactive antibody, RA45, increased $K_m$ less than 35% (from 256 to 344 nM), and $k_{cat}$ less than 47% (from 0.00605 to 0.00888 s$^{-1}$) (FIG. 4A and Table 3). Overall, the catalytic efficiency increased only 9% compared to enzyme alone ($k_{cat}/K_m$ of 23,600 to 25800 M$^{-1}$ s$^{-1}$). A non-cross reactive antibody, RA27, actually suppressed $k_{cat}/K_m$ by 370% (from 23,600 to 6330 M$^{-1}$ s$^{-1}$). Thus, the effect of cross-reactive antibodies on PAD4 activity is not due to direct effects on the active site, but lies almost entirely in their ability to shift the calcium sensitivity to a more physiological range.

Figure 3:
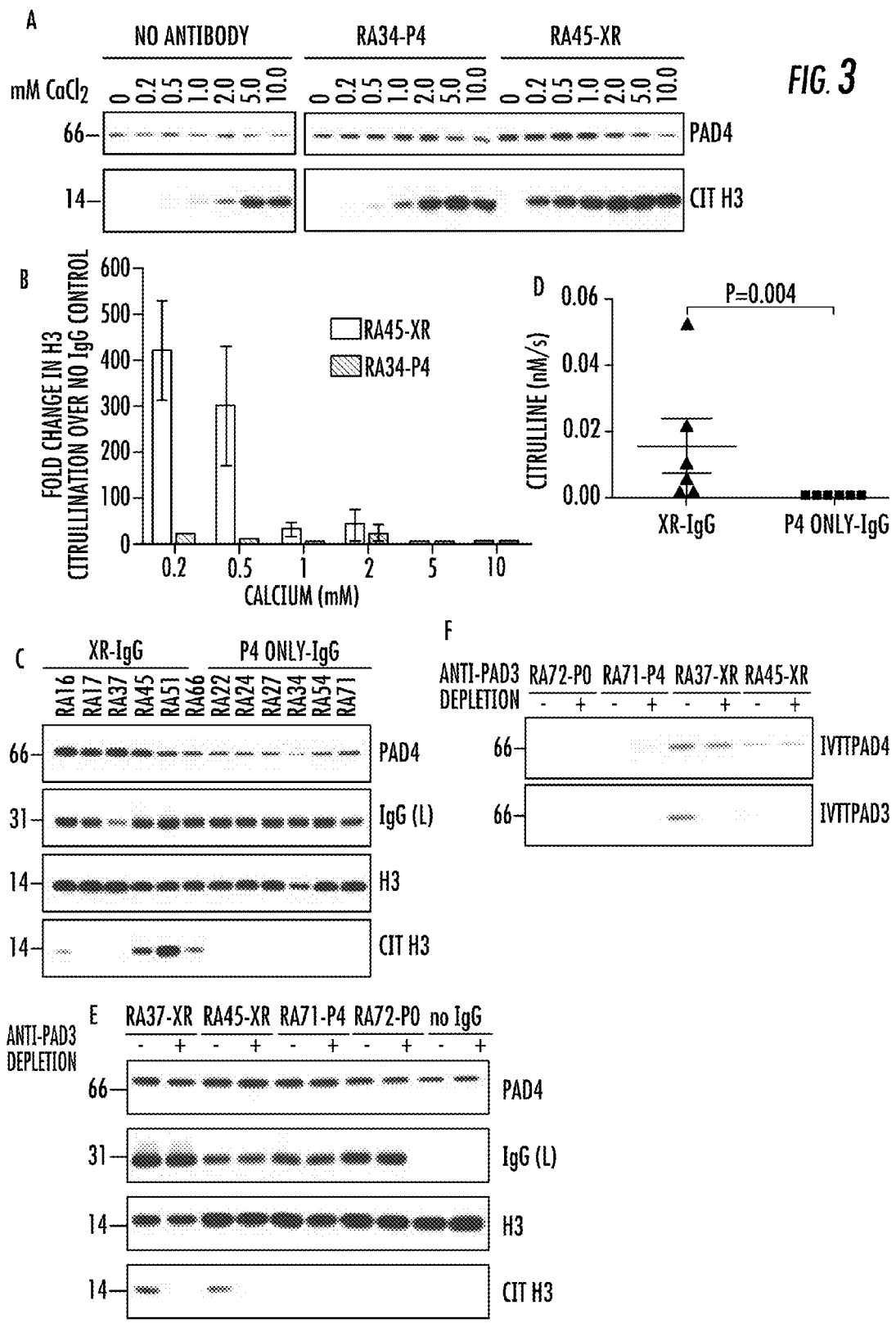
FIG. 3 shows that cross-reactive antibodies increase the calcium sensitivity of PAD4. PAD4 was pre-incubated with no antibody, anti-PAD4 only (RA34-P4), or PAD3/PAD4 cross-reactive (RA45-XR) IgG at 4° C. for 45 minutes prior to use in citrullination assays. (A) Calcium titrations were performed using a sub-saturating concentration of histone H3

In order to define the biochemical parameters affected by cross-reactive antibody binding to PAD4, several calcium titrations were performed as in FIG. 3A. Representative titrations are shown in FIG. 4C, where data were fit to the Hill equation; mean values from 2-4 experiments are compiled in Table 3. Cross-reactive antibodies profoundly influenced the amount of calcium required for half-maximal PAD4 activity ($K_{0.5}$). In the absence of antibody, supra-physiological $Ca^{2+}$ concentrations were required for optimal enzyme activity, with a $K_{0.5}$=3.3±0.8 mM. The prototypic cross-reactive antibody (RA45) produced a significant decrease in the $K_{0.5}$ to 0.5±0.1 mM (p=0.04), while an anti-PAD4 only antibody (RA34) did not (p=0.14) (Table 3). This shift in $K_{0.5}$ greatly enhanced catalytic activity at low calcium ion concentrations as observed in FIG. 3 A-D. These dramatic increases in activity are a consequence of the large Hill coefficient and cooperative nature of calcium binding, which ordinarily causes the enzyme to become active over an unusually narrow range of calcium ion concentrations.

In the absence of antibodies, PAD4 displayed the expected response, with a Hill coefficient (nominally representing the minimum number of calcium ions involved) of 4.3±0.4. The cross-reactive antibody, RA45, significantly decreased the Hill coefficient to 2.0±0.6 (p=0.03), suggesting a decrease in calcium-binding cooperativity (Table 4). Other cross-reactive antibodies tested revealed similar shifts in calcium-binding cooperativity and these changes were not observed in the presence of anti-PAD4 only antibodies. The smaller Hill coefficient for the cross-reactive antibody implies either a decrease in the number of calcium ions involved, or a decrease in their interaction factors, or both.

TABLE 4

Kinetic parameters for histone H3 calcium titrations.

| Histone H3 | no IgG | RA34-P4 | RA45-XR |
|---|---|---|---|
| $K_{0.5}$ Calcium (mM) | 3.3 ± 0.8 | 1.6 ± 0.2 | 0.5 ± 0.1 |
| Hill coefficient (n) | 4.3 ± 0.4 | 5.1 ± 0.1 | 2.0 ± 0.6 |

Data represents average of 2-4 independent experiments

Example 6

PAD3 cross-reactive AAs protect PAD4 from proteolysis by granzyme B. The observation that cross-reactive antibodies enhanced PAD4 activity by modulating calcium sensitivity suggested that they may act to stabilize regions of the protein ordinarily stabilized by calcium ion-binding. Although PAD4 is able to bind five calcium ions, two ions that bind in the C-terminal domain are vital for the formation of the active site and are required for citrullination of BAEE ($Ca_1$ and $Ca_2$). Three other calcium ions ($Ca_3$, $Ca_4$, and $Ca_5$) bind in a disordered region at the interface of the N- and C-terminal domains to create an alpha helix that is thought to be involved in protein-protein interactions and only minimally affect citrullination of BAEE. It follows that PAD3/PAD4 cross-reactive antibodies may stabilize this region, in turn reducing the requirement for high calcium ion concentrations to maintain the structure needed for interaction with macromolecular substrates.

Interestingly, $Ca_4$ is coordinated by aspartic acid at position 388 ($D^{388}$), and binding of this calcium ion contributes to stabilizing this ordinarily unstructured region of PAD4. $D^{388}$ is located within the sequence MGPD$^{388}$, a tetrapeptide which also satisfies the consensus for cleavage by the serine protease granzyme B (GrB). Since susceptibility to cleavage by GrB is a frequent feature of autoantigens, we addressed whether PAD4 was a GrB substrate. PAD4 was efficiently cleaved by GrB ($k_{cat}/K_m=1.09\times10^5$ M$^{-1}$ s$^{-1}$) generating two fragments, an N-terminal 45 kDa fragment and a C-terminal 30 kDa fragment (FIG. 7A). Cleavage was abolished by an aspartic acid to alanine mutation at position 388 (MGPD$^{388}$→MGPA$^{388}$), confirming that GrB cleaves at this site.

While PAD4 was efficiently cleaved by GrB at 0 and 0.2 mM calcium, cleavage was reduced by 33.6% in the presence of 2 mM calcium (FIG. 7B), likely due to known calcium ion-induced structural changes around $D^{388}$. Strikingly, pre-incubation of PAD4 with cross-reactive IgG, but not PAD4-only IgG, protected PAD4 from proteolysis at 0.2 mM (39.8-50.3% reduction in cleavage) (FIG. 7B, upper panel). This effect was also observed at 0 mM calcium, but to a lesser extent (16.8-19.5% reduction in cleavage). Importantly, proteolysis of a control substrate, nucleophosmin (B23), was unaffected by calcium or the presence of antibodies (FIG. 7B, lower panel). The protective effects of cross-reactive antibody and 2 mM calcium were not additive, suggesting that they may be operating through a similar mechanism. These results further support the proposal that cross-reactive antibodies induce the calcium-bound conformation of PAD4 necessary for optimal citrullination of macromolecular substrates, without the requirement for supraphysiologic calcium concentrations.

Although anti-PAD4 antibodies are associated with severe erosive RA in multiple studies, the potential mechanisms underlying this association remain obscure. Our serendipitous discovery of anti-PAD3 antibodies has defined a new RA subset with the most erosive, progressive arthritis. These PAD3/PAD4 cross-reactive antibodies have the striking ability to enhance the sensitivity of PAD4 to calcium, supporting citrullination of histone H3 at physiologically relevant calcium concentrations. We propose that this ability to activate PAD4 enzymatic activity has pathogenic consequences in RA.

Example 7

Anti-peptidylarginine deiminase 3/4 cross-reactive antibodies are associated with radiographic interstitial lung disease in rheumatoid arthritis, an effect potentiated by smoking.

Among the 176 RA patients studied in a subset of RA patients [60% female, 86% Caucasian, mean age 59±9 years, 11% current smokers, median RA duration=8 years, median DAS28=3.7], any CT-ILD was observed in 58 (33%). Anti-PAD3/4 cross-reactive antibodies were detected in 19 (11%) and 37 (21%) had antibodies directed against PAD4 alone. In univariate analysis, the frequency of any CT-ILD among those with anti-PAD3/4 was 68%, vs. 27 and 29% among those with anti-PAD4 only and neither reactivity, respectively (crude OR=5.39; p=0.001 for the comparison of anti-PAD3/4 vs. no anti-PAD) (FIG. 8). The association was stronger after adjustment for relevant demographic and RA disease/treatment confounders (FIG. 9A: adjusted OR=7.22; p=0.001). Anti-PAD3/4 antibodies were significantly associated with all CT-ILD predominant patterns (i.e. ground glass opacification, honeycombing, etc. . . . ) and quantitative ILD scores were significantly higher for the anti-PAD3/4 vs. the no anti-PAD group (median ILD score 2 vs. 0 units, respectively; p=0.020). The association of anti-PAD3/4 antibodies with CT-ILD was stronger in ever smokers than never smokers. Among never smokers, the adjusted frequency of any ILD was 39 vs. 17%, respectively, for those with vs. without anti-PAD3/4 (FIG. 9B, never smokers: OR=3.01; p=0.19) compared with 93 vs. 30%, respectively, for ever smokers with vs. without anti-PAD3/4 (FIG. 9B, ever smokers: OR=29.5; p=0.004, p-value for interaction<0.05).

The prevalence of CT-ILD was markedly higher among RA patients with anti-PAD3/4 antibodies, even after accounting for relevant confounders, particularly among ever smokers. Further mechanistic studies are needed to determine whether there is a biologic interaction between smoking and pulmonary hyper-citrullination facilitated by anti-PAD3/4 antibodies that contributes to ILD pathogenesis.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for monitoring the clinical effectiveness of a rheumatoid arthritis (RA) treatment in a subject undergoing said treatment, the method comprising:
   a) obtaining a sample comprising blood, plasma or serum from a subject;
   b) providing a substrate having a first capture probe bound thereto, wherein the capture probe comprises peptidyl arginine deiminase 3 (PAD3) protein or a portion or fragment thereof which comprises an antigen recognized by autoantibodies (AAs) present in the serum of subjects suffering from RA;
   c) contacting the substrate having the capture probe bound thereto with the sample from the subject;
   d) contacting the substrate having the capture probe bound thereto with the sample from the subject;
   e) measuring the amount of a complex of the capture probe and the autoantibodies formed by step d);
   f) providing a normal reference level sample comprising blood, plasma or serum;
   g) comparing the amount of a complex of the capture probe and the autoantibodies formed from the subject undergoing treatment to the amount of a complex of the capture probe and the autoantibodies formed from the normal reference level sample;
   h) identifying the subject undergoing treatment as having statistically significant severe RA when the amount of a complex of the capture probe and the autoantibodies formed from the subject is increased compared to the amount of a complex of the capture probe and the autoantibodies formed from the normal reference level sample;
   i) administering to the subject a treatment regimen for RA;
   j) repeating steps a) to g) above; and
   k) identifying the subject undergoing treatment as having statistically significant clinical effectiveness when the amount of a complex of the capture probe and the autoantibodies formed from the subject is decreased when compared to the amount of a complex of the capture probe and the autoantibodies formed from the normal reference level sample.

2. The method of claim 1, wherein
step (b) further comprises a second capture probe comprising peptidyl arginine deiminase 4 (PAD4) protein or a portion or fragment thereof which comprises an antigen recognized by autoantibodies present in the serum of subjects suffering from RA;
step (e) further comprises measuring the formation of a complex of the first and second capture probes and the autoantibodies;
step (g) further comprises comparing the amount of the cross-reactive complex of both capture probes formed from the subject undergoing treatment to the amount of a complex of the capture probe and the autoantibodies formed from the normal reference level sample; and
step (k) further comprises identifying the subject undergoing as having statistically significant clinical effectiveness when the amount of the cross-reactive complex of both first and second capture probes formed from the subject suspected of having severe RA is decreased compared to the amount of the cross-reactive complex of both first and second capture probes formed from the normal reference level sample.

3. The method of claim 1, wherein said method is an enzyme immunoassay method.

4. The method of claim 1, wherein said method is a radioimmunoassay method.

5. The method of claim 1, wherein said method is an immunoblotting method.

6. The method of claim 1, wherein said capture probe is bound to said substrate with a binding reagent.

7. The method of claim 3, further comprising an anti-human antibody.

8. The method of claim 4, further comprising an anti-human antibody.

9. The method of claim 1, wherein said capture probe is bound to said substrate with a binding reagent.

* * * * *